United States Patent
Laser et al.

(10) Patent No.: US 10,955,067 B2
(45) Date of Patent: Mar. 23, 2021

(54) METHODS AND SYSTEMS FOR ENHANCED MICROFLUIDIC PROCESSING

(71) Applicant: Wave 80 Biosciences, Inc., San Francisco, CA (US)

(72) Inventors: Daniel Laser, San Francisco, CA (US); Amy Droitcour, San Francisco, CA (US); Hailemariam Negussie, San Francisco, CA (US); William Behnke-Parks, San Francisco, CA (US)

(73) Assignee: Wave 80 Biosciences, Inc., San Francisco, CA (US)

( * ) Notice: Subject to any disclaimer, the term of this patent is extended or adjusted under 35 U.S.C. 154(b) by 1300 days.

(21) Appl. No.: 14/771,651

(22) PCT Filed: Mar. 3, 2014

(86) PCT No.: PCT/US2014/020029
§ 371 (c)(1),
(2) Date: Dec. 8, 2015

(87) PCT Pub. No.: WO2014/137940
PCT Pub. Date: Sep. 12, 2014

(65) Prior Publication Data
US 2016/0008811 A1    Jan. 14, 2016

Related U.S. Application Data

(60) Provisional application No. 61/771,708, filed on Mar. 1, 2013.

(51) Int. Cl.
*G01N 1/30* (2006.01)
*C12Q 1/02* (2006.01)
(Continued)

(52) U.S. Cl.
CPC ...... *F16K 99/0051* (2013.01); *B01F 11/0071* (2013.01); *B01F 13/0059* (2013.01);
(Continued)

(58) Field of Classification Search
CPC ......... G01N 33/54366; G01N 21/6428; G01N 1/30; G01N 2021/6432; G01N 2021/6439;
(Continued)

(56) References Cited

U.S. PATENT DOCUMENTS 5,965,001 A * 10/1999 Chow .............. G01N 27/44713
204/600
6,277,257 B1    8/2001 Paul et al.
(Continued)

FOREIGN PATENT DOCUMENTS

EP    0816837 A1    1/1998
JP    2000-513813 A    10/2000
(Continued)

OTHER PUBLICATIONS

European Extended Search Report, European Application No. 14761250.1, dated Jul. 26, 2016, 10 pages.
(Continued)

*Primary Examiner* — Gailene Gabel
(74) *Attorney, Agent, or Firm* — Goodwin Procter LLP

(57) ABSTRACT

Methods and systems are provided for a microfluidic cartridge including a high performance actuator useful for analyte detection, labeling and analysis. Microfluidic processing systems are to carry out chemical or biochemical reactions, or sequences of reactions, with small volumes (typically between 1 microliter and 10 milliliters) of reactants and products. A microfluidic processing system can comprise a network of tubes interfaced with discrete components such as valves and sensors, or an integrated device
(Continued)

made of plastic, glass, metal, or other materials, or a combination of materials, with components such as valves and sensors built into the device and connected by flow passageways formed in the material.

59 Claims, 25 Drawing Sheets

(51) Int. Cl.
| | |
|---|---|
| F16K 99/00 | (2006.01) |
| B01L 3/00 | (2006.01) |
| C12Q 1/6806 | (2018.01) |
| C12Q 1/6844 | (2018.01) |
| C12N 15/10 | (2006.01) |
| G01N 21/64 | (2006.01) |
| G01N 33/543 | (2006.01) |
| B01F 11/00 | (2006.01) |
| B01F 13/00 | (2006.01) |
| B82Y 30/00 | (2011.01) |

(52) U.S. Cl.
CPC ..... *B01L 3/50273* (2013.01); *B01L 3/502738* (2013.01); *B82Y 30/00* (2013.01); *C12N 15/1006* (2013.01); *C12N 15/1013* (2013.01); *C12Q 1/02* (2013.01); *C12Q 1/6806* (2013.01); *C12Q 1/6844* (2013.01); *C12Q 1/6846* (2013.01); *F16K 99/0017* (2013.01); *G01N 1/30* (2013.01); *G01N 21/6428* (2013.01); *G01N 33/54366* (2013.01); *B01L 3/502784* (2013.01); *B01L 2200/0647* (2013.01); *B01L 2200/12* (2013.01); *B01L 2300/0645* (2013.01); *B01L 2300/0654* (2013.01); *B01L 2300/0816* (2013.01); *B01L 2300/0858* (2013.01); *B01L 2300/0864* (2013.01); *B01L 2300/0867* (2013.01); *B01L 2300/12* (2013.01); *B01L 2400/0415* (2013.01); *B01L 2400/0418* (2013.01); *B01L 2400/0478* (2013.01); *B01L 2400/0487* (2013.01); *F16K 2099/008* (2013.01); *F16K 2099/0084* (2013.01); *F16K 2099/0086* (2013.01); *F16K 2099/0094* (2013.01); *F16K 2099/0096* (2013.01); *G01N 2021/6432* (2013.01); *G01N 2021/6439* (2013.01); *G01N 2021/6441* (2013.01)

(58) Field of Classification Search
CPC ...... C12Q 1/02; C12Q 1/6806; C12Q 1/6844; C12Q 1/6846; C12N 15/1013; C12N 15/1006; B01L 5/50276; B01L 5/502738; B01L 3/502784; B01L 3/502738; B01L 2200/0647; B01L 2300/0864; B01L 2300/0645; B01L 2400/0654; B01L 2400/0415; B01L 2400/0418; B01L 2400/0487

See application file for complete search history.

(56) References Cited

U.S. PATENT DOCUMENTS

| | | | | |
|---|---|---|---|---|
| 6,391,622 | B1* | 5/2002 | Knapp | .................. B01L 3/0262 204/450 |
| 2002/0179445 | A1 | 12/2002 | Alajoki et al. | |
| 2004/0241004 | A1 | 12/2004 | Goodson et al. | |
| 2005/0034990 | A1 | 2/2005 | Crooks et al. | |
| 2005/0233198 | A1 | 10/2005 | Nuzzo et al. | |
| 2007/0170062 | A1 | 7/2007 | Lauks | |
| 2009/0155877 | A1 | 6/2009 | Iliescu et al. | |
| 2009/0253196 | A1 | 10/2009 | Ikeya et al. | |
| 2011/0000560 | A1 | 1/2011 | Miller et al. | |
| 2011/0114492 | A1 | 5/2011 | Anex et al. | |
| 2012/0236299 | A1* | 9/2012 | Chiou | ............... B01L 3/502715 356/301 |
| 2015/0268029 | A1* | 9/2015 | Rowat | .................. G01N 29/022 435/34 |

FOREIGN PATENT DOCUMENTS

| | | |
|---|---|---|
| JP | 2001-502790 A | 2/2001 |
| JP | 2004-508837 A | 3/2004 |
| JP | 2004-340962 A | 12/2004 |
| JP | 2006-022807 A | 1/2006 |
| JP | 2011-509658 | 3/2011 |
| JP | 2012-508894 A | 4/2012 |
| JP | 2012-511156 A | 5/2012 |
| JP | 2012-527622 A | 11/2012 |
| JP | 2012-251927 | 12/2012 |
| JP | 2013-520298 A | 6/2013 |

OTHER PUBLICATIONS

PCT International Search Report and Written Opinion, PCT Application No. PCT/US2014/020029, 25 pages. (2014).
PCT International Search Report and Written Opinion, PCT Application No. PCT/US2014/019590, dated Jun. 5, 2014, 18 pages.
PCT Written Opinion of the International Preliminary Examining Authority, PCT Application No. PCT/US2014/019590, dated May 8, 2015, 5 pages.
Zeng, S. et al., "Electroosmotic Flow Pumps with Polymer Frits," Sensors and Actuators B: Chemical, Feb. 2002, pp. 209-212, vol. 82, No. 2-3.
Yao, S. et al., "Porous Glass Electroosmotic Pumps: Theory," Journal of Colloid and Interface Science, Dec. 2003, pp. 133-142, vol. 268, No. 1.
Chen, C-H. et al., "A Planar Electroosmotic Micropump," Journal of Microelectromechanical Systems, Dec. 2002, pp. 672-683, vol. 11, No. 6.
Yao, S. et al., "Electroosmotic Pumps Fabricated From Porous Silicon Membranes," Journal of Microelecromechanical Systems, Jun. 2006, pp. 717-728, vol. 15, No. 3.
Burgreen, D. et al., "Electrokinetic Flow in Ultrafine Capillary Slits1," The Journal of Physical Chemistry, 1964, pp. 1084-1091, vol. 68, No. 5.
Laser, D.J., "Temporal Modulation of Electroosmotic Micropumps," Proceedings of IMECE 2006, 2006 ASME International Mechanical Engineering Congress and Exposition, Fluids Engineering in Micro- and Nano-Systems VII, 2006, p. 67-72.
Frey, J. et al., "Modeling Electric Fields in Slit Capillary Array Fluidic Actuators with Complex Electrode Geometrics," presented at the COMSOL User Conference, 2012, 4 pages.
Laser, D.J. et al., "Silicon Electroosmotic Micropumps for Integrated Circuit Thermal Management," The 12$^{th}$ International Conference on Solid-State Sensors, Actuators and Microsystems (Transducers '03), IEEE, Jun. 8-12, 2003, pp. 151-154.
United States Office Action, U.S. Appl. No. 14/771,636, dated Jun. 15, 2017, 23 pages.
United States Restriction Requirement, U.S. Appl. No. 14/771,636, dated Mar. 24, 2017, 6 pages.
Japanese First Office Action, Japanese Application No. 2015-560397, dated Dec. 4, 2017, 10 pages.

* cited by examiner

METHODS AND SYSTEMS FOR ENHANCED MICROFLUIDIC PROCESSING

CROSS REFERENCE TO RELATED APPLICATIONS

This application claims the benefit of U.S. Provisional Application No. 61/771,708, filed on Mar. 1, 2013, which is hereby incorporated in its entirety by reference.

This application is related to U.S. Provisional Application No. 61/771,694, filed on Mar. 1, 2013, which is hereby incorporated in its entirety by reference.

STATEMENT REGARDING FEDERALLY SPONSORED RESEARCH OR DEVELOPMENT

This invention was made with government support under NIH contract HHSN272200900029C and NIH grant 2R44AI073221, awarded by the National Institutes of Health. The government has certain rights in the invention.

BACKGROUND OF THE INVENTION

Field of the Invention

The invention relates to methods and systems for moving and processing fluid through an assay system.

Description of the Related Art

Microfluidic processing systems are to carry out chemical or biochemical reactions, or sequences of reactions, with small volumes (typically between 1 microliter and 10 milliliters) of reactants and products. A microfluidic processing system can comprise a network of tubes interfaced with discrete components such as valves and sensors, or an integrated device made of plastic, glass, metal, or other materials, or a combination of materials, with components such as valves and sensors built into the device and connected by flow passageways formed in the material.

Conventional microfluidic processing systems use reciprocating displacement pumps, peristaltic effects, syringe pumps, surface tension effects, body forces on magnetic beads from external or internal magnetic field sources, vacuum manifolds, electrokinetic effects, electrochemical effects, or a combination of these to carry out chemical or biochemical reactions or sequences of reactions.

Flows in microfluidic processing systems are typically associated with dominance of viscous effects over inertial effects, referred to as a low Reynolds number regime. Many applications of microfluidic processing systems involve one or more high-molecular-weight reactants with correspondingly low binary diffusivities. For example, molecular dynamic simulations indicate that the ribonucleic acid chain of approximately 9800 bases which constitutes the genomic material of the human immunodeficiency virus (HIV), with a molecular weight of $3.1 \times 10^6$ daltons, has a diffusivity in water of approximately $D = 2 \times 10^{-12}$ $m^2$ $s^{-1}$, such that, in 10 minutes, one-dimensional diffusion is associated with displacement of only 50 microns. The combination of the dominance of viscous effects over inertial effects and the relatively slow diffusivities of reactants of high interest imposes a need for fluid mechanical mechanisms for macroscopically mixing two or more solutions in microfluidic systems.

Small volumes of gases are often found in microfluidic systems, having been either introduced as part of the process to be carried out or arising inadvertently, such as when an expansion or contraction of a fluid passageway in the direction of flow tends to trap bubbles during filling. A volume of gas in a microfluidic system can act as a low-pass filter with respect to mechanical forcing functions acting on the system. This is sometimes referred to as fluidic capacitance. Tubing can also be a source of fluidic capacitance.

The tendency of trapped air to act as a low-pass filter creates an incentive to locate a fluidic actuator in close physical proximity to the fluid volume on which said actuator is to apply force and do mechanical work.

In some applications of microfluidic systems, there is a need for the reactions to take place within fluid passageways which can be discarded after a single use. For example, in infectious disease diagnostics, a microfluidic system used to process a body fluid sample can be considered a biohazardous waste after completion of the assay. The very high negative impact of contamination between production runs creates an incentive for microfluidic systems used for antibody purification to be fully disposable after a single use. Many types of microfluidic actuators, such as piezoelectric actuators and electromagnetic actuators, are too expensive to include in a microfluidic cartridge for a single use. Piezoelectric actuators and electromagnetic actuators require mechanical energy transfer into the cartridge and can be prone to failure associated with misalignment of the actuator and the cartridge. Actuation mechanisms, such as electrochemical gas generation and surface tension-based actuation, can be economically built into cartridges, but are associated with slow response times, low power output, lack of range, and other limitations.

There is a need for microfluidic systems which can carry out rapid macroscopic mixing of one or more reactants. A fast response time and high power of a fluidic actuator are important for mixing two or more fluids or for reacting two or more species in a mixture in the cartridge. Current microfluidic actuators have limitations of low fluid power generation capacity, sustaining power and slow response times. While electroosmotic flow generation can be associated with high power and fast response times, in some cases, samples cannot be transported through an EO microfluidic device because particles in the sample could block the EO device, and the fluid would be adversely affected by the high electric fields inside the EO device.

The present invention addresses these and other shortcomings of the prior art.

SUMMARY OF THE INVENTION

The invention comprises a microfluidic processing system including a plurality of fluid passageways, at least one junction connecting the plurality of fluid passageways, at least two mechanisms for fluid transport including at least one high-performance fluidic actuator. The high-performance fluidic actuator has a fluid power generation capacity of at least $10^{-8}$ watts, is capable of sustaining the power for at least 30 seconds, and has a response time for fluid power generation of less than 10 seconds.

In some embodiments, the microfluidic processing system is an integrated system, referred to as a cartridge. In some embodiments, the cartridge has a displaced volume less than or equal to five hundred cubic centimeters, or less than or equal to fifty cubic centimeters.

In some embodiments, the high-performance fluidic actuator is capable of transducing electrical power directly into fluidic power. In some embodiments, operation of the high-performance fluidic actuator does not comprise a transfer of mechanical energy from an external device to the at least one high-performance fluidic actuator.

In some embodiments, the response time for power generation is less than 2 seconds, less than 0.2 seconds, or less than 0.04 seconds. In one embodiment, the actuator is capable of acting on at least 10 microliters of liquid, such that the liquid flows through a fluidic resistance associated with a pressure drop of at least 1 kPa at a flow rate of at least 0.1 mL per minute.

In another embodiment, the high-performance actuator is coupled to a pulse generator or other controlled time-varying voltage source. In some embodiments, the high-performance fluidic actuator is capable of producing fluidic power through electrokinetic effects. In some embodiments, the electrokinetic effect is electroosmotic flow. The electroosmotic flow may be generated within a slit capillary or within the interstices of a slat structure within each at least one fluidic actuator.

In another embodiment, the electroosmotic flow is generated within a bed of packed beads, a monolithic porous structure, or an array of cylindrical channels within each of the fluidic actuators.

In some embodiments, the microfluidic cartridge includes an opening for receiving a starting material into the network of fluid passageways. The opening can be closed with a plug or a capping element. The plug or capping element is capable of receiving a fluid conduit and sealing shut when the fluid conduit is withdrawn. In other embodiments, the fluid conduit is capable of being received by the plug or capping element and can comprise a needle, a tube, a rigid fluid conduit, or a semi-rigid fluid conduit. The plug or capping element can comprise an elastomeric material. In another embodiment, the plug or capping element has a closing mechanism.

In other embodiments, the cartridge includes a controller capable of controlling power delivery from a power source to the high-performance fluidic actuator. The cartridge can include a power source operatively coupled to the at least one high-performance fluidic actuator. The power source can be located in an external device and coupled to the cartridge by an electrical connection. In some embodiments, the power source is electrical or pneumatic. The power source can be a battery that can be located inside the cartridge. In other embodiments, the battery can be located in an external device and coupled to the cartridge by an electrical connection.

The cartridge can include a second opening for receiving a processing fluid that is coupled to the network of fluid passageways. The processing fluid can be contained within the network of fluid passageways. The processing fluid can include a first reagent capable of lysing a cell or a cellular organelle. The first reagent comprises a detergent or other surfactant. In another embodiment, the first reagent comprises an enzyme, such as a lysozyme.

In some embodiments, the processing fluid comprises a homogenization solution capable of homogenizing a tissue sample or other heterogeneous biological material.

In other embodiments, the processing fluid comprises a solution capable of diminishing or eliminating biological activity of a living cell, tissue, or organism. The processing fluid can comprise a glass bead or other solid material capable of causing mechanical disruption of the starting material. In some embodiments, the processing fluid can comprise a glycogen or other polysaccharide. The processing fluid can include a carrier RNA.

In some embodiments, the cartridge includes a third opening for receiving an actuator fluid that is coupled to the high-performance fluidic actuator. The actuator working fluid can be situated within the at least one high-performance fluidic actuator.

In another embodiment, a portion of the network of fluidic passageways comprises a second reagent. The second reagent can include a silica bead, a particle, or a paramagnetic bead. The second reagent can also be a fluorescent bead or a fluorescent molecule. The second reagent can be a chemiluminescent molecule, such an alkaline phosphatase substrate, or a lanthanide or a lanthanide chelate. In other embodiments, the second reagent comprises a monoclonal or a polyclonal antibody, and the monoclonal or polyclonal antibody can be linked to a signaling molecule.

The second reagent can be an oligonucleotide probe or primer, or a combination of probes or a combination of primers. The oligonucleotide probe specifically can bind to a defined region of the genetic material of human immunodeficiency virus, a hepatitis C virus, a hepatitis B virus, a M. tuberculosis bacterium, a C. trachomatis bacterium, an influenza virus, respiratory syncytial virus, or another virus of the human respiratory tract. The oligonucleotide probe can bind to a defined region of the DNA or RNA of a cancer gene. In some embodiments, the oligonucleotide probe is labeled, and the label can be a fluorescent or a luminescent signaling molecule or a quencher thereof, an aptamer, a photosensitizer molecule, a photoactive indicator precursor molecule, or a photosensitizer molecule and a photoactive indicator precursor molecule.

In some embodiments, the photosensitizer molecule and the photoactive indicator precursor molecule comprise: at least one sensitizer label particle comprising one or more sensitizer agents, one or more sensitizer oligonucleotides, and a matrix for co-locating such sensitizer agents and sensitizer oligonucleotide(s); and at least one emitter label particle comprising one or more emitter agents, one or more sensitizer oligonucleotides, and a matrix for co-locating such emitter agent(s) and emitter oligonucleotide(s). The photosensitizer molecule is capable in an excited state of generating a singlet oxygen molecule. The photoactive indicator precursor molecule is capable of reacting with a singlet oxygen molecule to form a photoactive indicator.

In other embodiments, the second reagent can be a quantum dot or other crystalline semiconductor particle. The second reagent can be a nucleic acid-specific fluorescent or luminescent dye for sequence-independent measurement of nucleic acids. The second reagent can be a molecule capable of participating in Förster Resonance Energy Transfer (FRET) or other resonance energy transfer process. In another embodiment, the second reagent comprises a labeled protein, a labeled nucleic acid, or a labeled carbohydrate species for measurement of a specific cellular compound.

The second reagent can include a solution having a dye for specific or non-specific labeling of a cell. The second reagent can include a primer, a probe, a combination of a primer and a probe, or an enzyme capable of catalyzing a polymerase chain reaction, a transcription-mediated amplification, a nucleic acid sequence-based amplification, or another chemical reaction for amplifying at least one specified nucleic acid sequence. The enzyme can be a DNA polymerase, a reverse transcriptase, an RNA polymerase, an RNAse H, a DNA helicase, or a recombinase.

In another embodiment, the starting material comprises a fluid phase, a fluid-laden matrix, or a solid phase. The starting material can be blood, sputum, or other bodily fluid. The starting material can include a biological tissue, a raw material or intermediary for a pharmacological agent or a vaccine, an agricultural product, soil or another environmental sample.

In one embodiment, the cartridge includes a first fluid passageway comprising a first substance and a second fluid passageway comprising a second substance, wherein said first fluid passageway and said second fluid passageway form a junction in said microfluidic cartridge. In another embodiment, the junction is a T-junction or a Y-junction. In yet another embodiment, the junction allows formation of one or more microfluidic droplets generated from merging of said first and second substances from said first and second fluid passageways. In other embodiments, the one or more droplets each comprise an analyte or a reagent. In another embodiment, the one or more droplets each comprise at least one primer and an enzyme capable of catalyzing a polymerase chain reaction, a transcription-mediated amplification, a nucleic acid sequence-based amplification, or another chemical reaction for amplifying at least one target nucleic acid sequence. In some embodiments, the one or more droplets each comprise a label. In other embodiments, the first or second substances comprise a processing fluid. In another embodiment, the one or more droplets each comprise a cell.

In another embodiment, the cartridge includes a plurality of fluid passageways comprising different temperature zones for performing stages of an amplification reaction. In one embodiment, a plurality of fluids are combined in said plurality of fluid passageways to trigger a labeling or hybridization reaction.

The invention comprises a system including the microfluidic cartridge described above and an apparatus comprising a power source and adapted in some embodiments for sourcing electrical power to the microfluidic cartridge. In other embodiments, the microfluidic cartridge has an onboard power source. The apparatus is further adapted for sensing an indicator of assay outcome. The sensor can sense visible light or another type of electromagnetic radiation generated within the cartridge. In some embodiments, the apparatus is further adapted for sensing a location or a distribution of paramagnetic beads within the cartridge. The apparatus can be adapted for sensing electron spin nuclear magnetic resonance or other physical property of a species within the cartridge.

Another embodiment includes a method comprising providing a first fluid to a channel connected to a plurality of fluid passageways, including at least one junction among such fluid passageways, in a microfluidic cartridge. The microfluidic cartridge includes at least one high-speed microfluidic actuators having a fluid power generation capacity of at least $10^{-8}$ watts and capable of sustaining the power for at least 30 seconds and a response time for power generation of less than 10 seconds. The method includes operating the microfluidic actuators in a time-varying manner, such that the first fluid and a second fluid are introduced into the network of fluid passageways to generate alternating plugs of fluids, wherein a length of each plug volume is less than 5 times the smallest average diameter among such fluid passageways. The high-speed microfluidic actuator can produce fluid power by an electrokinetic effect. The electrokinetic effect can be generated by an electroosmotic flow generated within an array of slits, a packed bead bed, or a monolithic porous structure.

The method includes labeling a subset of cells within the first fluid with a labeling molecule or a labeling particle within the second fluid specific for at least one type of molecule in a cell membrane. The method can include dying a cell in the first fluid with a cell permeating dye contained in the second fluid.

In other embodiments, the method includes labeling a subset of DNA or RNA contained within the first fluid with a photosensitizer molecule or a photoactive indicator precursor molecule or a combination thereof contained in the second fluid. The method can also include labeling a subset of DNA or RNA contained within the first fluid with a lanthanide chelate contained in the second fluid. The method includes lysing a cell or other biological material within the first fluid with a detergent or other surfactant contained in the second fluid. The detergent can be sodium lauryl sulfate, hexadecyltrimethylammonium bromide, or another cationic detergent.

In another embodiment, the method includes lysing a cell or other biological material within the first fluid with an enzyme. The enzyme can be a lysozyme. The method further comprises homogenizing a tissue sample or other heterogeneous biological material from the first fluid. The method also includes reducing the biological activity of a living cell, tissue, or organism in the first fluid. The reducing of biological activity step can include using a highly basic solution, such as sodium hydroxide or sodium hypochlorite.

The method further includes lysing a cell or other biological material in the first fluid with a glass bead or other solid material for mechanical disruption in the second fluid. The method includes mixing a swab or a porous matrix with the first fluid and releasing soil or other environmental samples bound within the swab or the porous matrix.

In one embodiment, the first fluid comprises a dendritic cell, and the method includes pulsing the dendritic cells to induce an element of an immune response to insult.

The method can include producing a pharmacological substance or a vaccine. The method includes increasing the bioactivity of a pharmacological substance. The method can also include binding a DNA or an RNA molecule contained within the first fluid to glycogen or silica. The method also includes purifying the glycogen-complexed or co-precipitated DNA and RNA or purifying the DNA or RNA molecule bound to a silica bead or a silica-containing structure. The method includes eluting the DNA and RNA from the glycogen or silica bead or silica-containing structure.

The method also includes detecting a presence or an absence of an analyte in the first fluid. The detecting comprises sensing visible light or another type of electromagnetic radiation from a chemiluminescent or fluorescent molecule coupled to the analyte. Detecting can include sensing a location or a distribution of paramagnetic beads coupled to the analyte or sensing nuclear magnetic resonance or other physical properties of a species coupled to the analyte.

In one embodiment, the method also includes steps for generating a plurality of microdroplets in the plurality of fluid passageways. In another embodiment, the plurality of microdroplets are formed by pulsating at least two fluids, wherein pulsating is generated by a plurality of high-speed microfluidic actuators in the microfluidic cartridge. The method can also include detecting a presence or an absence of an analyte in each of the plurality of microdroplets. In another embodiment, the method includes performing an amplification reaction in each of the plurality of microdroplets by moving the plurality of microdroplets through a plurality of temperature zones in the microfluidic cartridge. In yet another embodiment, the method includes detecting a presence of a target amplicon in each of the plurality of microdroplets. The method also includes measuring a melting temperature ($T_m$) of a target nucleic acid molecule in each of said plurality of microdroplets. In one embodiment, the method includes performing a melting temperature ($T_m$) analysis of genetic divergence of a virus RNA from a reference strain.

BRIEF DESCRIPTION OF THE SEVERAL VIEWS OF THE DRAWINGS

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE INVENTION

Overview

Figure 1:
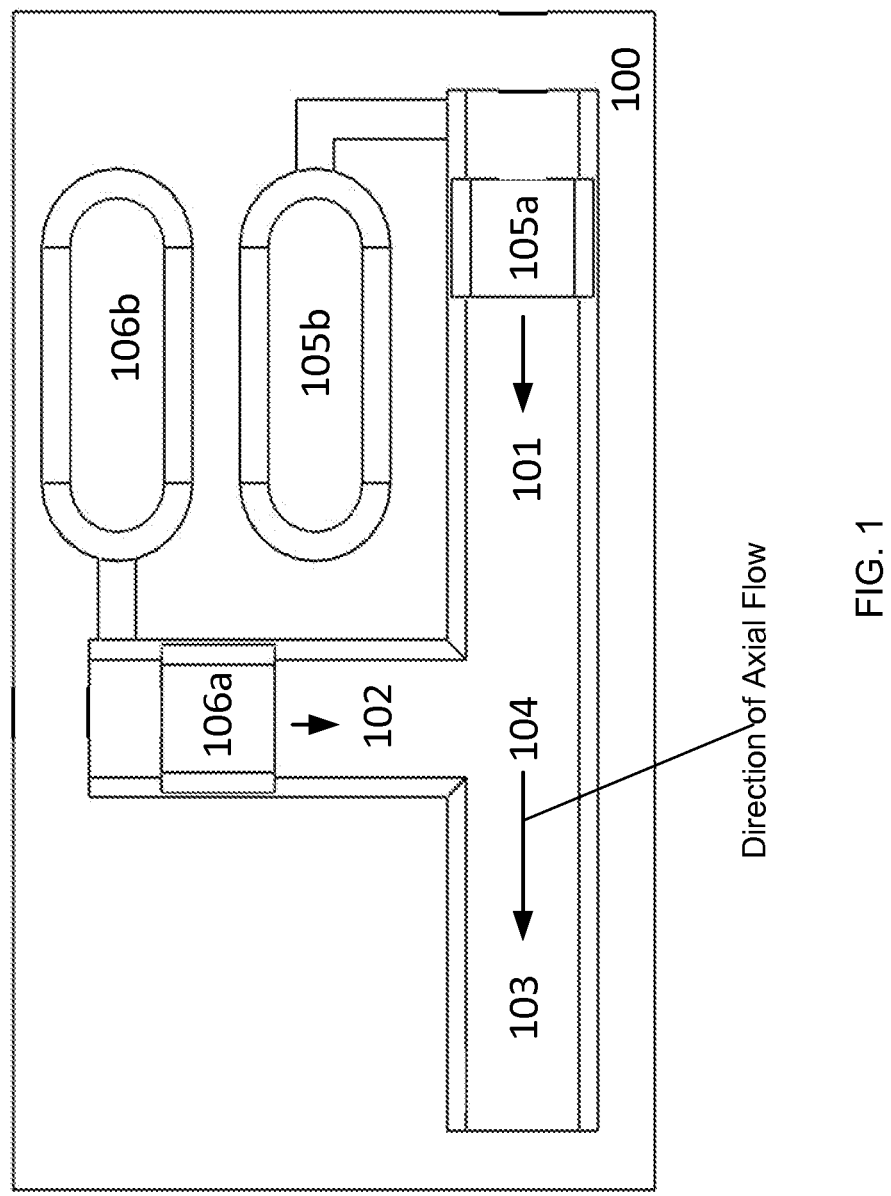
FIG. 1 is an example of a top-down, cut-away view of the interior of a microfluidic cartridge, according to one embodiment of the invention.

Flows in microfluidic processing systems are typically associated with dominance of viscous effects over inertial effects, referred to as a low Reynolds number regime [1], [2]. Many applications of microfluidic processing systems involve one or more high-molecular-weight reactants [3], [4], with correspondingly low binary diffusivities. For example, molecular dynamic simulations [5] indicate that the ribonucleic acid chain of approximately 9800 bases which constitutes the genomic material of the human immunodeficiency virus (HIV), with a molecular weight of $3.1\times 10^6$ daltons, has a diffusivity in water of approximately $D=2\times10^{-12}$ $m^2$ $s^{-1}$, such that, in 10 minutes, one-dimensional diffusion is associated with displacement of only 50 microns. The combination of the dominance of viscous effects over inertial effects and the relatively slow diffusivities of reactants of high interest imposes a need for fluid mechanical mechanisms for macroscopically mixing two or more solutions in microfluidic systems.

When an aqueous solution contacts a surface such as glass or silica, the surface becomes negatively charged due to the depronation of surface silanol groups. An electrical double layer forms as a result of the depronation. The surface charge attracts dissolved counter-ions and repels co-ions, resulting in a charge separation. The Debye length is the characteristic thickness of the double layer. The mobile ions in the diffuse counter-ion layer are driven by an externally applied electrical field, and the moving ions drag along bulk liquid through viscous force interaction.

The average velocity of electroosmotic flow generated between two wide parallel surfaces by the application of an axial electric field Ex is:

$$\bar{v} = -\frac{a^2}{3\mu}\frac{dp}{dx} - \frac{\varepsilon\zeta}{\mu}E_x[1 - G(\alpha, \kappa\alpha)]$$

where a is one-half the separation distance between the two pumping surfaces, μ is the fluid viscosity, dp/dx is the pressure gradient counter to the flow, ε is the fluid permittivity, ζ is the zeta potential, α is the ionic energy parameter, and G is the correction term for the thickness of the double layer. The wide parallel surfaces become charged, attracting counter-ions and repelling co-ions, to form a charge double layer. The outer layer of ions of the double layer is mobile. Applying an axial electric field exerts forces on the mobile ions and electromigration of the mobile ions drag the bulk fluid through viscous interaction. The zeta potential characterizes the effect of the surface condition on the electroosmotic flow. The zeta potential is an empirical parameter associated with the net excess of surface charge-balancing ions near the surface/fluid interface.

Definitions

Terms used in the claims and specification are defined as set forth below unless otherwise specified.

"Electroosmotic flow" refers to the movement of liquid induced by an applied potential across a fluid conduit. The fluid conduit can be any porous material, capillary tube, membrane, substrate, microchannel or passageway for allowing the flow of liquid. The electric potential can be applied between any two parallel surfaces.

A "microfluidic actuator" or "fluidic actuator" refers to a component that converts electrical power or another readily stored or generated form of energy into fluid power, meaning the application of force on a mass of fluid to transport said mass of fluid through a pressure gradient [6].

"Taylor dispersion" refers to the transport and spreading of a mass of solute in laminar flow through a long, straight tube or other similar flow passageway, such mass of solute initially confined within a plug (or a plurality of plugs) within the flow, such plugs having axial dimensions on the same order as the tube cross-section [2].

"Zeta potential" refers to an empirical or semi-empirical parameter included in many mathematical models of electroosmotic flow, where, other factors being equal, a higher absolute value of a zeta potential is generally associated with higher flow rates and/or higher maximum back pressures [7], [8].

It must be noted that, as used in the specification and the appended claims, the singular forms "a," "an" and "the" include plural references unless the context clearly dictates otherwise.

Overview of Microfluidic System

The invention includes a microfluidic system, such as a cartridge or similarly enclosed fluid processing device. In some embodiments, the microfluidic cartridge has no moving mechanical parts and eliminates failure modes associated with sliding contacts, fluidic fittings, etc. In one embodiment, the microfluidic cartridge runs on battery power and incorporates EO fluidic actuation without the need of an external syringe pump or some other means of fluidic actuation. In another embodiment, the microfluidic cartridge includes an internal mechanism for moving fluid that is pressurized by a microfluidic actuator.

In some embodiments, the microfluidic cartridge is small in size and can be used with a hand-held, portable device. For example, the cartridge may be less than 40 cm$^3$ in volume (2 cm×2 cm×10 cm=40 cm$^3$). In addition, the cartridge can have a displacement volume of 50-500 cc's. For example, the cartridge can be small enough to fit in a person's hand and sized for manufacturing in large quantities at low cost.

The microfluidic system includes a network of fluidic passageways. The passageways can include pipes, tubes, enclosed channels, or other enclosed structures for holding and allowing transport of fluids. The fluidic passageways can be loaded with small quantities of at least two different fluids. The fluids can have a volume of less than 10 milliliters each, for example. In one embodiment, at least one of the fluids is loaded into the cartridge at or around the time of operation through a port. In other embodiments, fluids are pre-loaded into the cartridge.

The network of fluidic passageways can be connected by one or more junctions. Each junction joins two or more fluidic passageways and can be configured in various arrangements and designs.

The microfluidic cartridge includes at least two microfluidic actuators, and at least one microfluidic actuator is a high performance microfluidic actuator. The at least one high performance microfluidic actuator has a fluid power generation capacity of at least 10$^{-8}$ watts, is capable of sustaining power for at least 30 seconds, and has a response time for power generation of less than 10 seconds. The network of fluidic passageways is in fluid communication with the microfluidic actuators.

The microfluidic system may be a cartridge made of plastic, glass, or other materials. Fluid passageways and other features within the cartridge may be produced by machining, hot-embossing, injection molding, or other means. The cartridge may be assembled from multiple pieces by thermal bonding, laser welding, ultrasonic welding, or through the use of epoxies or pressure-sensitive adhesives or other adhesive means.

The microfluidic actuators of the invention may operate through the generation of electroosmotic flow.

The microfluidic actuators of the invention may be made from silicon, glass, plastic, or other materials. In some embodiments, the microfluidic actuator is made from a single-crystal silicon wafer coated with multiple layers of silicon oxide and silicon nitride, with the openings in the single-crystal silicon wafer made by a photolithographic feature definition process followed by time-multiplexed inductively coupled plasma (TM-ICP) etching, also known as deep-reactive ion enhanced (DRIE) etching [9]. The microfluidic actuators can be produced from a single-crystal silicon wafer by a simple, one-step photolithographic process. These microfluidic actuators are economical for incorporation into single-use microfluidic cartridges for a variety of applications.

In some embodiments, the microfluidic cartridge is designed to dock or couple with an instrument for analyzing or processing the fluids or samples inside the cartridge. The instrument can include various detection or monitoring components for analyzing the fluids or samples, and can include a power supply or electrical circuitry for providing energy to the cartridge.

In some embodiments, electrical power source and associated circuitry is built into the cartridge, which operates without connection to external hardware.

In FIG. 1, an example of a microfluidic cartridge 100 is shown from a top-down, cut-away perspective of the interior of the cartridge 100. The microfluidic cartridge includes a first fluidic passageway 101, a second fluidic passageway 102, a third fluidic passageway 103, and a junction 104 that connects the first, second, and third fluidic passageways. The microfluidic cartridge includes a first pressure source and a second pressure source. Each of the pressure sources can be a microfluidic actuator 105b, 106b, at least one of which is a high performance microfluidic actuator. In some embodiments, the actuators may also include one or more pistons or piston-like elements, 105a and 106a. In some embodiments, the piston-like elements 105a and 105b may be plugs of solid material which form a perimeter seal with the inside of the fluid passageways within which said plugs travel.

In one embodiment, the microfluidic actuator 105b, 106b acts on a processing fluid contained within a fluidic passageway 101, 102 via the piston or piston-like element 105a and 106a. For example, operation of the first microfluidic actuator 105b pushes the actuator's piston 105a forward. The movement of the piston 105a pressurizes a fluid within the fluidic passageway 101, causing such fluid to travel toward the junction 104. Similarly, operation of the second microfluidic actuator 106b pushes the second piston 106a forward. The movement of the piston 106a pressurizes a fluid within the fluidic passageway 102, causing such fluid to travel toward the junction 104. The two processing fluids are joined and mixed at the junction 104.

In other embodiments, pistons 105a, 106a are not present in the cartridge as solid elements. The actuator fluid is contained within or in fluidic contact with the microfluidic actuator 105b, 106b and is separated from the processing fluid in the fluidic passageway by a plug of a barrier fluid. In some embodiments, the barrier fluid is air or another gas. Fluidic movement of the actuator fluid causes the air plug to become pressurized and to move forward, which in turn, pressurizes and generates fluidic movement of the processing fluid in the fluidic passageway. The function of the air plug as a piston is enhanced through surface tension effects. In some embodiments, the interior surface of the fluid passageway within which the air plug travels is hydrophobic and free of sharp axial features conducive to the flow of the actuator working fluid along the wall of the passageway past the air plug. In some embodiments, a plug of an immiscible fluid functions as a piston. In some embodiments, there is no plug of fluid separating the actuator fluid from the processing fluid, and the actuator fluid is in direct contact with the processing fluid in the fluidic passageway, but does not mix with the processing fluid (e.g., two immiscible fluids). The movement of the actuator fluid causes corresponding pressurization and movement of the processing fluid.

Moving fluid through the fluidic passageways toward the junction 104 results in at least one fluid passing through the junction 104 and into the third fluidic passageway 103. For fluidic passageways with cross-sectional dimensions less than 10 mm and containing liquid phase fluids, the flow of fluid within the passageways 101, 102 and junction 104 can be characteristically laminar.

The first and second fluidic actuators 105b and 106b can be operated so that the velocities and flow rates of the fluids within the first and second fluid passageways 101 and 102 are nearly invariant over time, constant and result in semi-discrete fluid laminae in the region of the fluidic passageway 103 immediately beyond the junction 104. Where there are a series of cross-sections of fluid passageways over a distance of several millimeters beyond the junction 104 in the direction of flow (referred to as the axial direction), the concentration of a first fluid can be nearly 100% in one region of the cross-section, and the concentration of a second fluid is nearly 100% in another region. The persistence of such spatial localization as a function of the axial distance from the junction 104 is approximately inversely proportional to the diffusivities of the species in the processing fluids.

Deviations from the laminar flow operation described above, such as alternating plugs of processing fluid, can result from the time-varying action of one or more of the microfluidic actuators with corresponding time-varying pressurization and flow of one or more of the processing fluids. In one example, the first microfluidic actuator 105b is operated with a square wave voltage input at a given frequency and a duty cycle less than 100%, and the second microfluidic actuator 106b is operated with a square wave voltage input at the same frequency and at a duty cycle less than 100%, with the first actuator square wave out of phase with the second.

Figure 2:
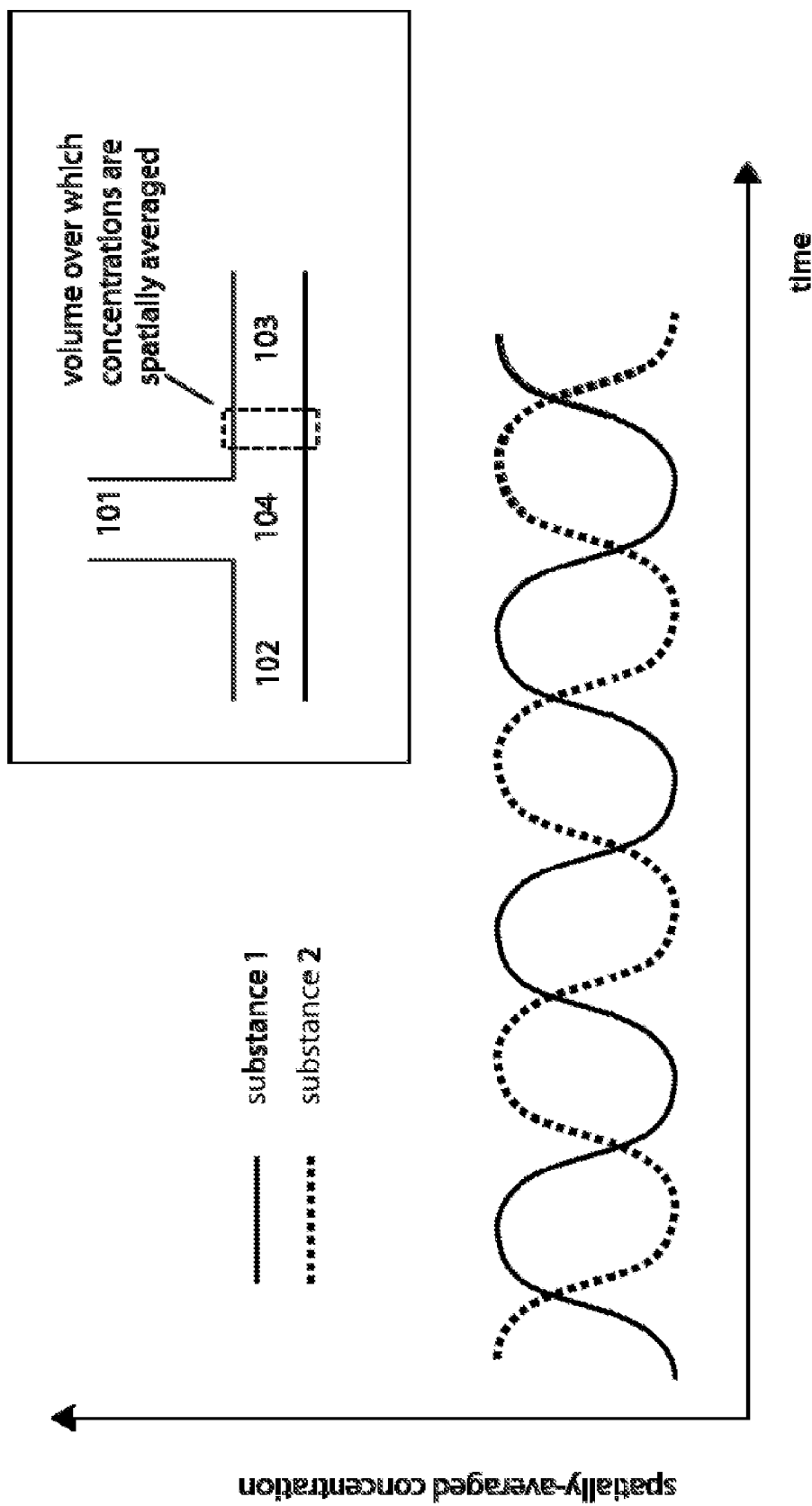
FIG. 2 illustrates the processing of fluids each containing a single dissolved substance and the concentrations of each of the two dissolved substances as spatially averaged across a short channel section of the fluid passageway downstream of junction and plotted as a function of time, according to one embodiment of the invention.

FIG. 2 is an example illustrating that the processing fluids are aqueous solutions each containing a single dissolved substance and the concentrations of each of the two dissolved substances are spatially averaged across a short channel section of the fluid passageway 103 downstream of junction 104 and plotted as a function of time. The out-of-phase operation of the actuators results in a sequential injection of alternating plugs of fluids contained in the fluid passageways 101 and 102. Because of predominance of viscous forces over inertial forces, molecular diffusion can be the primary mechanism by which chemical and biochemical constituents of two fluids intermingle when such fluids are combined within a microfluidic cartridge. Spatially non-uniform distributions of fluids can shorten the distances over which such diffusion takes place, speeding chemical and biochemical reactions.

Figure 3:
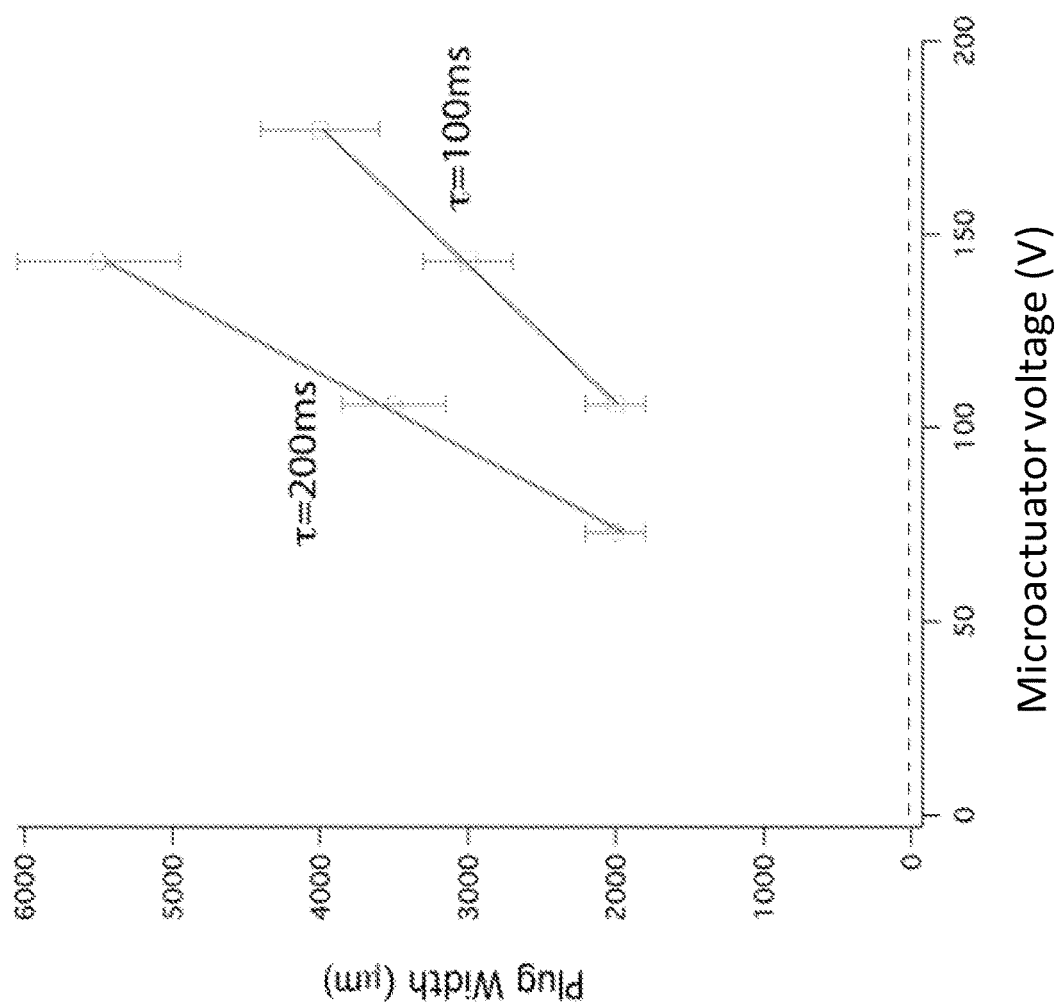
FIG. 3 illustrates a graph showing a functional relationship between the maximum voltage and plug width for two fluids downstream of the junction, according to one embodiment of the invention.

FIG. 3 is an example of a functional relationship between the maximum voltage, duty cycle, and period of microactuator operation and plug width of the two species downstream of the junction 104. The data plotted in FIG. 3 were collected with a cartridge of the invention where the fluid passageways are cylindrical with diameter approximately 1 mm. The microfluidic actuators transduce electrical power into fluid power through the generation of electroosmotic flow in the interstices within a slat structure comprising silicon coated with thin films of silicon nitride and silicon oxide. One of the two solutions contains a fluorescent species, such that plug widths could be monitored by epifluorescent microscopy with a CCD camera. Voltages ranging from 75 V to 175 V were applied to the two actuators operating out of phase with a 50% duty cycle and on-state durations of 100 and 200 milliseconds. As shown, fluid plugs measuring 2 mm axial direction could be produced. Downstream mixing of the short plugs can occur through Taylor dispersion.

Figure 4:
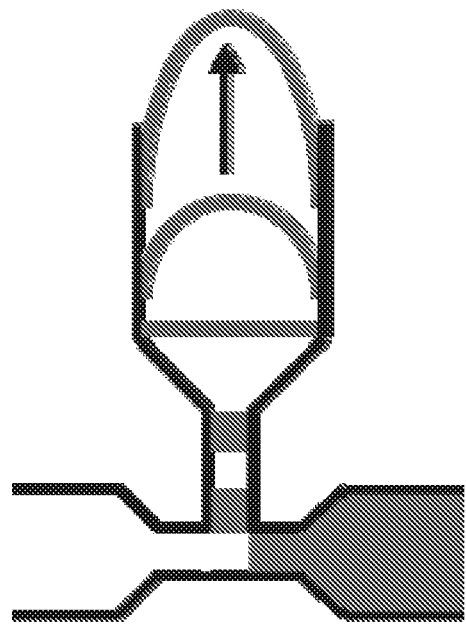
FIG. 4 illustrates various flow passageway junction geometries, according to one embodiment of the invention.
Figure 4:
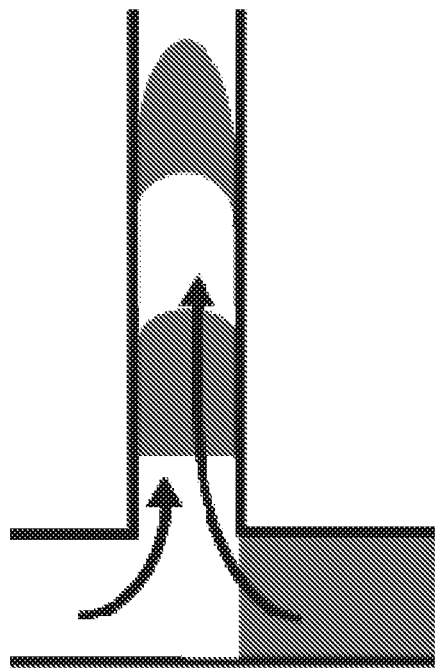

The minimum axial dimension of fluid plugs can be constrained by the cross-sectional dimensions of the flow passageways at the junction. FIG. 4 is an example of a flow passageway junction geometry in which the flow passageways neck down, or decrease in cross-sectional dimension, in the region immediately adjoining the junction.

Figure 5:
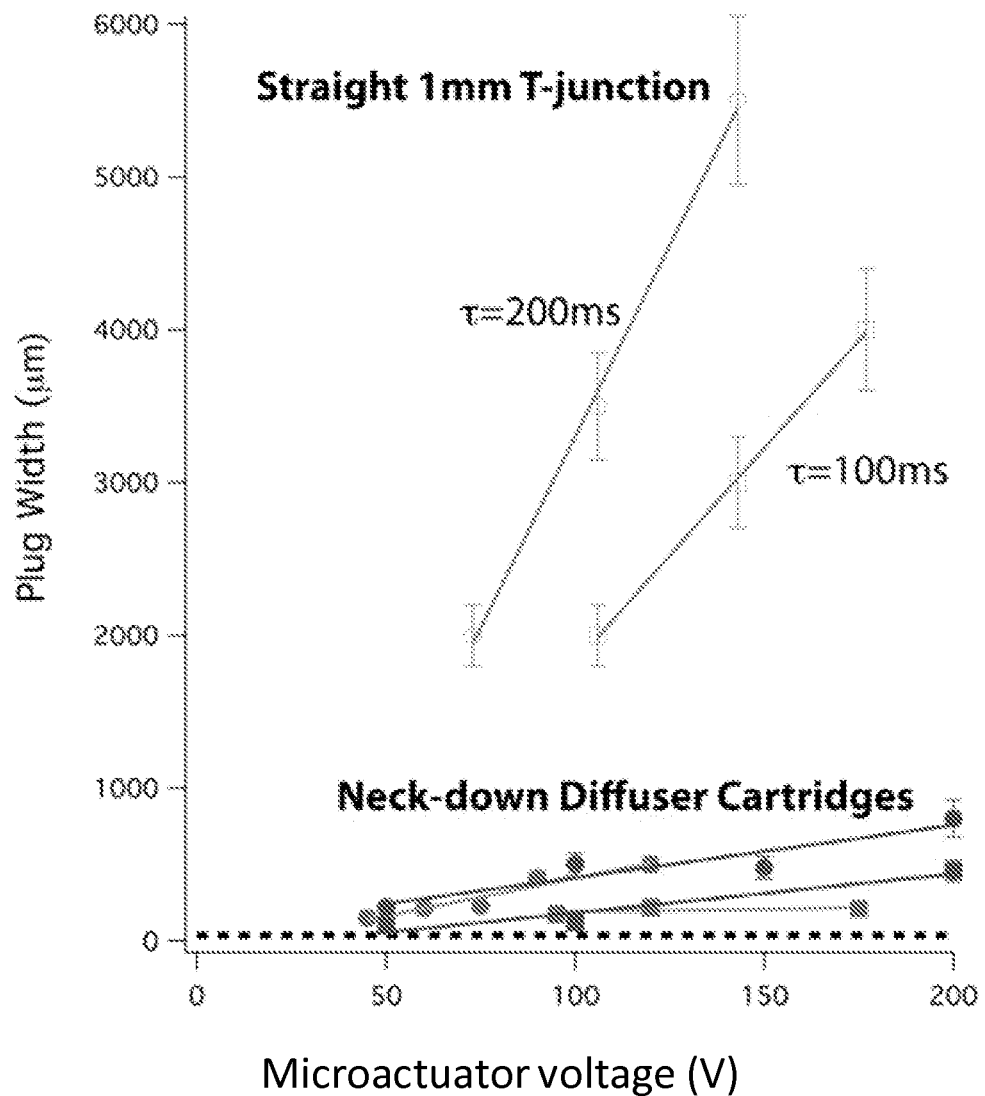
FIG. 5 illustrates a graph showing the plug width vs. microactuator voltage for microfluidic cartridges, according to one embodiment of the invention.

FIG. 5 shows that a combination of the neck-down geometry and fast microactuator response can produce very short plugs of fluid.

Figure 6:
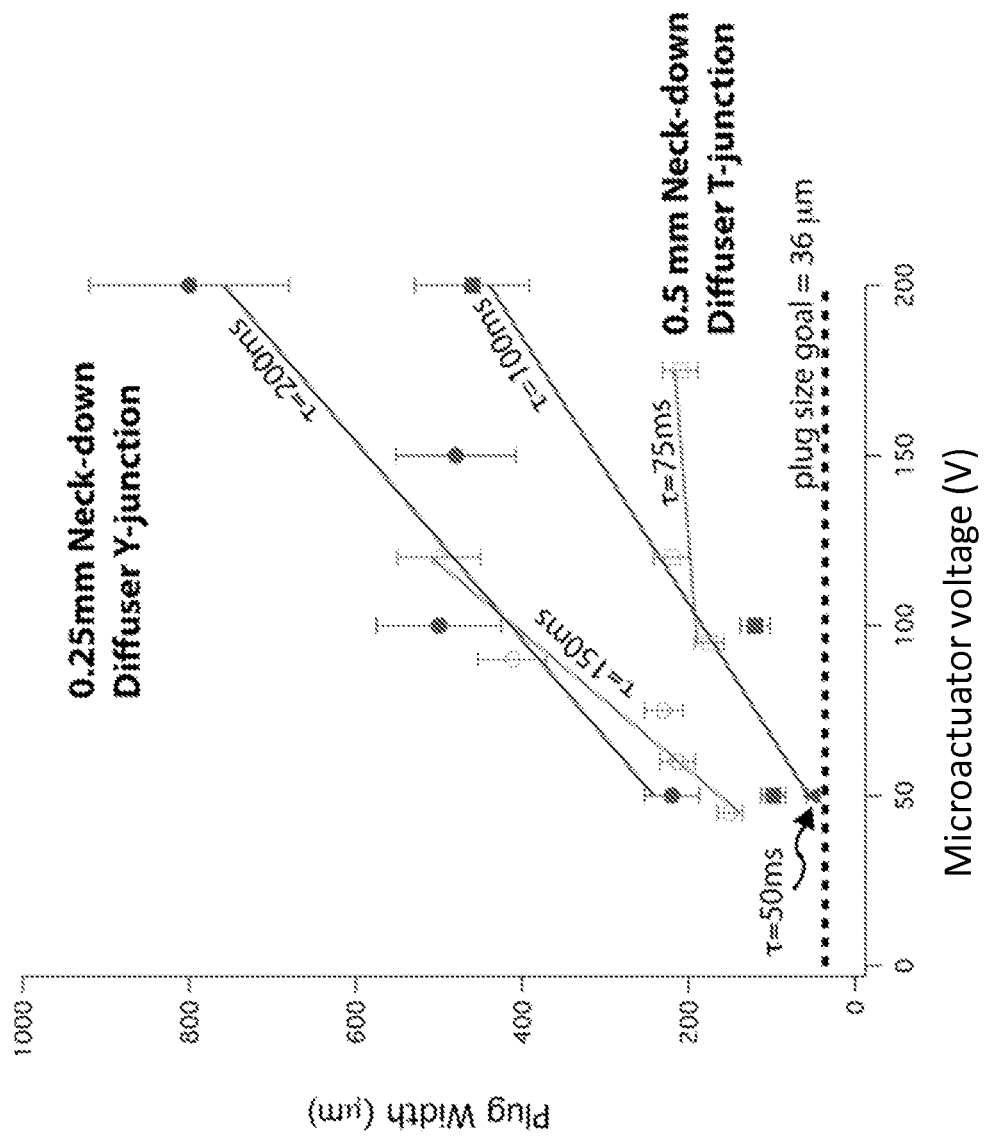
FIG. 6 illustrates a graph showing the plug width vs. microactuator voltage for a various neck-down diffuser junction designs of the short-plug-width region, according to one embodiment of the invention.

FIG. 6 illustrates a graph showing the plug width vs. microactuator voltage for a various neck-down diffuser junction designs of the short-plug-width region of FIG. 4. A 50 millisecond on-state duration with a junction where the channels neck down from 1 mm diameter to 0.25 mm diameter produced plugs less than 50 microns in the axial direction. With plugs of this size, a first solution containing a relatively slow-diffusing species such as 200 nm diameter beads will fully mix with a second solution in less than 10 minutes.

For greater control over differential fluid transport and/or to mix multiple fluids together, multiple microfluidic actuators can be used with multiple channels and junctions for moving and combining fluids. Each microfluidic actuator 105b, 106b is fluidly connected to an actuator fluid and generates flow of a processing fluid. For example, two microfluidic actuators 105b, 106b can generate mixing of two processing fluids. Next, the mixture can be joined with a third fluid in another fluidic passageway using the fluidic pressure of two additional microfluidic actuators.

In some embodiments, the microfluidic cartridge 100 is loaded with two fluids, one in the first fluidic passageway 101 and the other in the second fluidic passageway 102. In some embodiments, the fluids are loaded at or around the time of manufacture of the microfluidic cartridge. The microfluidic cartridge 100 can include actuator fluid in fluidic contact with each of the microfluidic actuators 105b, 106b.

In other embodiments, the microfluidic cartridge 100 is loaded with a reagent in a fluidic passageway 101, 102. The reagent can be a fluid phase form, a dried reagent, or attached to a surface or wall of the fluidic passageway (e.g., a bead or particle). In some embodiments, the reagent is in a processing fluid and includes a detergent or other surfactant for lysing a cell or cellular organelle. The reagent can be an enzyme, such as a lysozyme. In other embodiments, the reagent is an antibody, protein, peptide, oligonucleotide, or particle for binding, hybridizing or interacting with an analyte in the sample or processing fluid. Other examples of reagents are described in detail below.

Figure 7:
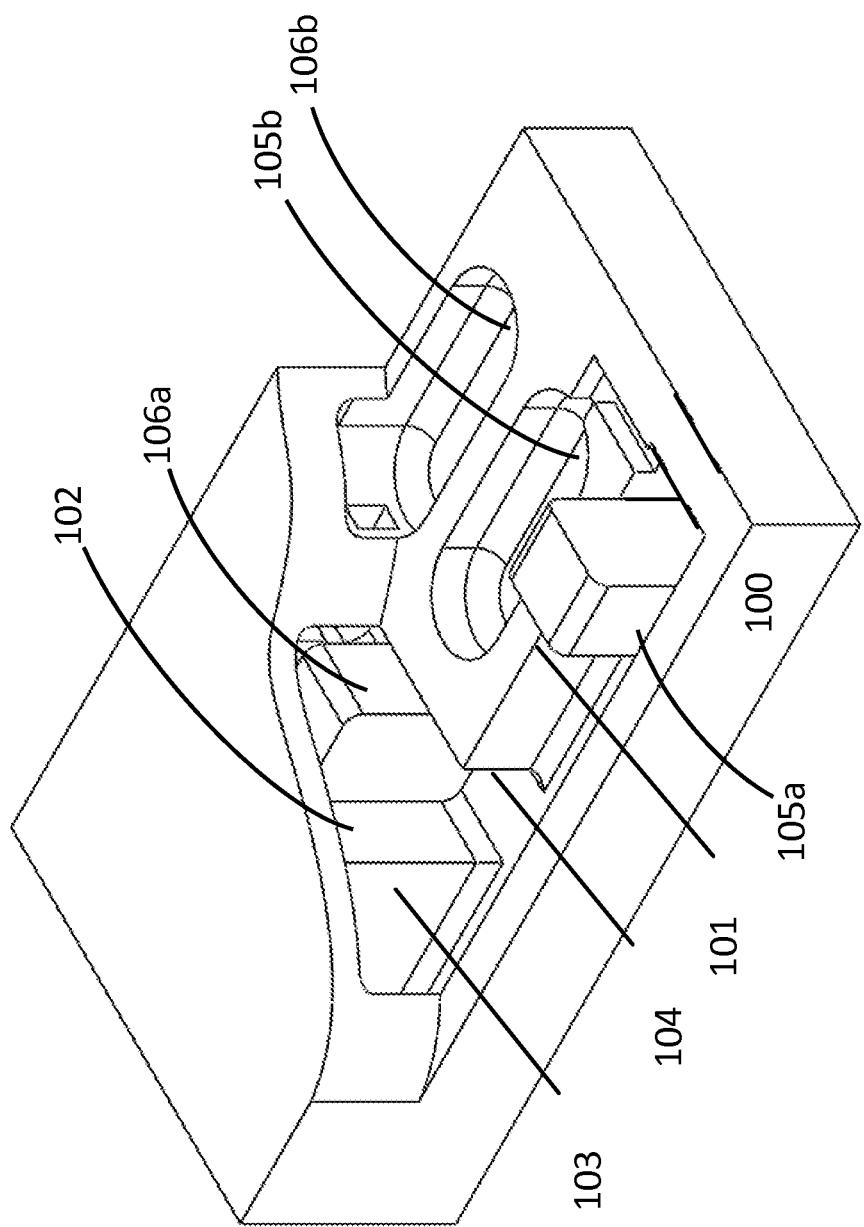
FIG. 7 is an example of a side, cut-away view of the microfluidic cartridge, according to one embodiment of the invention.

FIG. 7 is an example of the microfluidic cartridge 100 of FIG. 1, shown from a side perspective of the interior of the cartridge 100. As in FIG. 1, the microfluidic cartridge includes a first fluidic passageway 101, a second fluidic passageway 102, a third fluidic passageway 103, and a junction 104, where the first and second fluidic passageways meet. The microfluidic cartridge includes a first fluidic actuator 105b and a second fluidic actuator 106b. The cartridge also includes one or more pistons or piston-like elements 105a and 106a that are pushed forward by the first and second fluidic actuators 105b, 106b.

Figure 8:
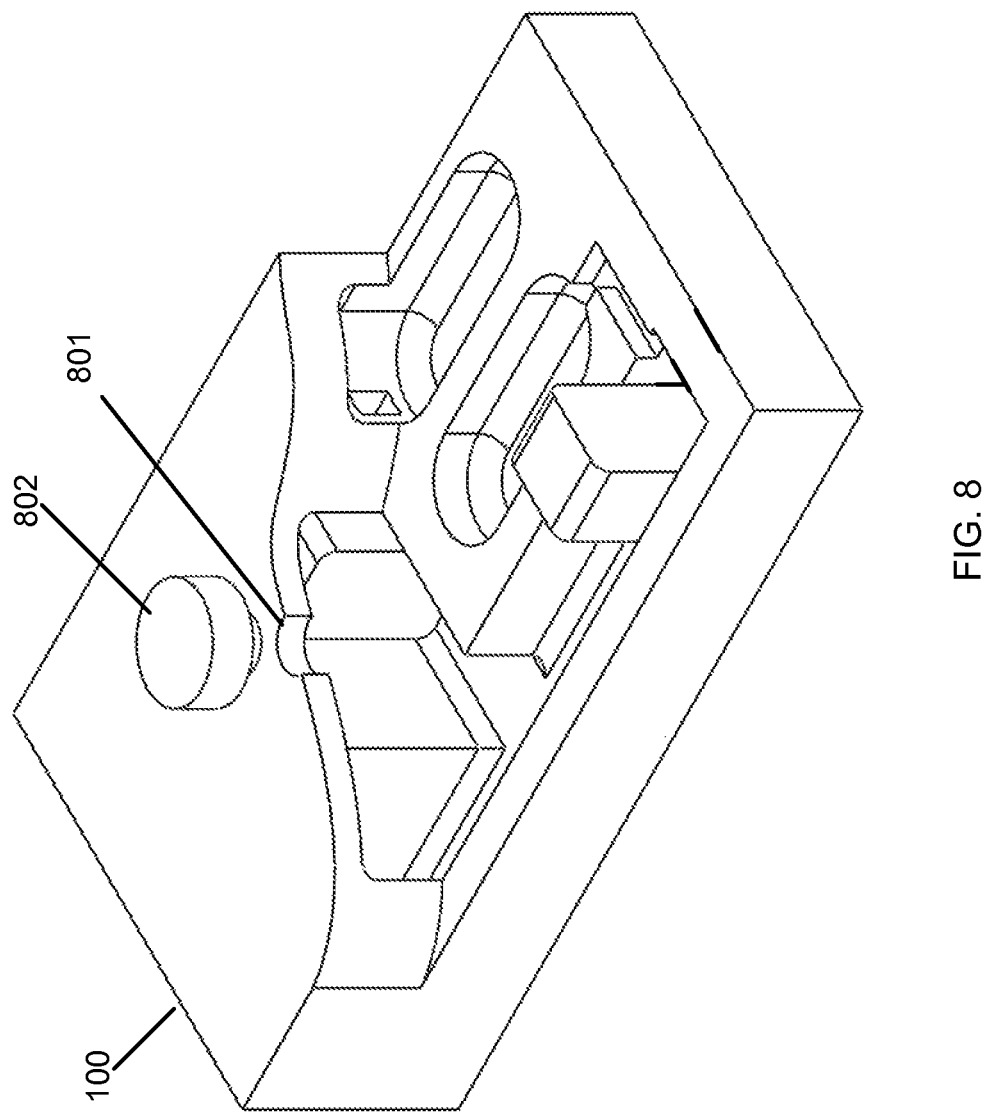
FIG. 8 is an example of a side, cut-away view of the microfluidic cartridge, including an opening, according to one embodiment of the invention.

Referring now to FIG. 8, an opening 801 is shown on the top of the microfluidic cartridge 100, which can be used to admit a starting material, sample, or fluid for subsequent processing. The opening is connected to the network of fluidic passageways. The opening can be connected to a fluidic passageway for processing the starting material. To prevent fluid from flowing out of the opening 801 during operation of the microfluidic cartridge 100, the opening 801 can have a cap, capping element, plug or other type of closure 802. In some embodiments, the opening 801 can seal closed by a mechanism, such as a pneumatic valve. The opening 801 can be self-sealing through a passive mechanism, such as a perforated elastomeric structure that can elastically deform when acted upon by a narrow conduit, such as a syringe. In other embodiments, the plug or capping element 802 is capable of receiving a fluid conduit and sealing shut when the fluid conduit is withdrawn. The fluid conduit can be a needle, a tube, a rigid fluid conduit, or a semi-rigid fluid conduit. The opening can also be closed by a thermopheumatic effect, an electromagnetic effect or an electrostatic effect.

Figure 9:
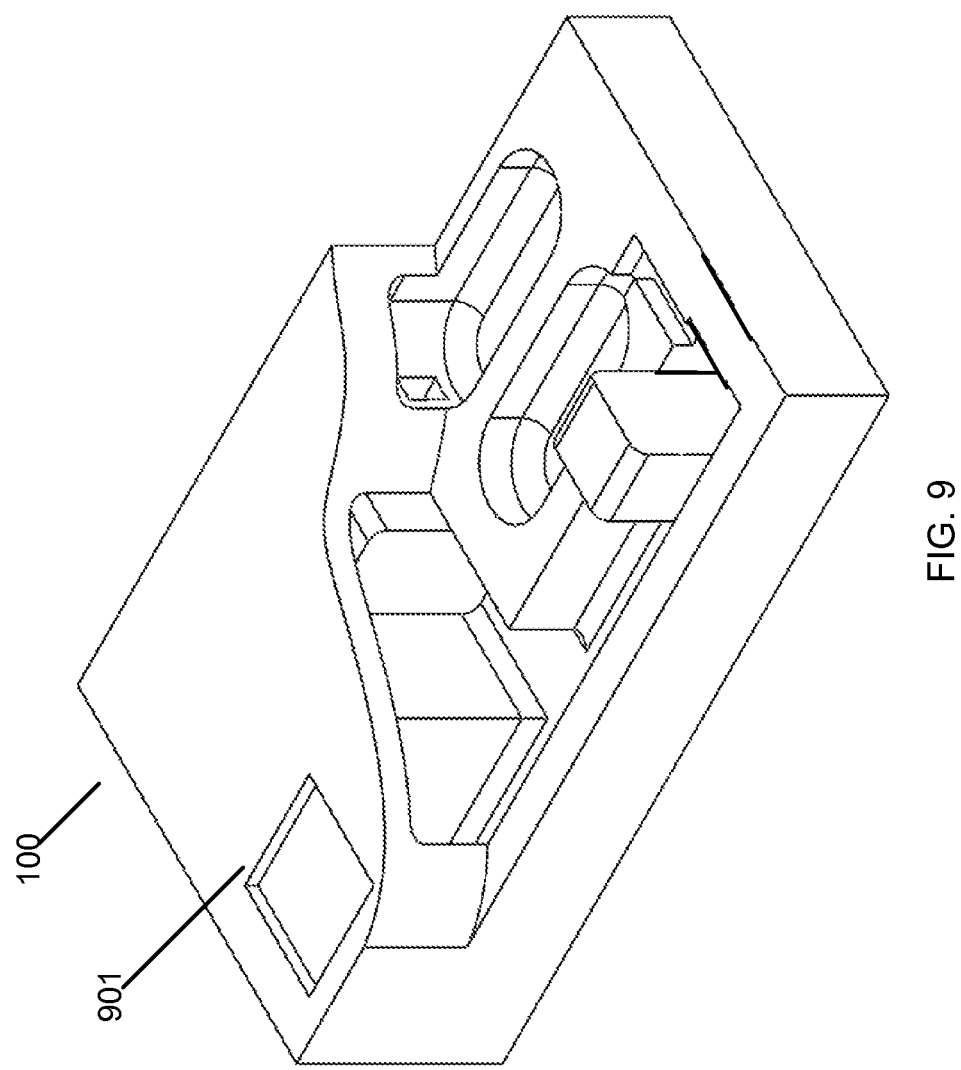
FIG. 9 is an example of a side, cut-away view of the microfluidic cartridge, including viewing window, according to one embodiment of the invention.

In one embodiment, the microfluidic cartridge 100 includes at least one component or module to facilitate monitoring of a fluid process or for analyzing the output of a fluid process. In FIG. 9, the microfluidic cartridge 100 includes an optically transparent region 901 that allows the viewing or monitoring of the fluid in the third fluidic passageway 103, such as the color, opacity, and other such physical properties of the fluid. The transparent region 901 can allow analysis of the fluid within the fluidic passageway 103, using techniques such as fluorescence, chemiluminescence, or other analytical methods, such as those described herein.

Figure 10:
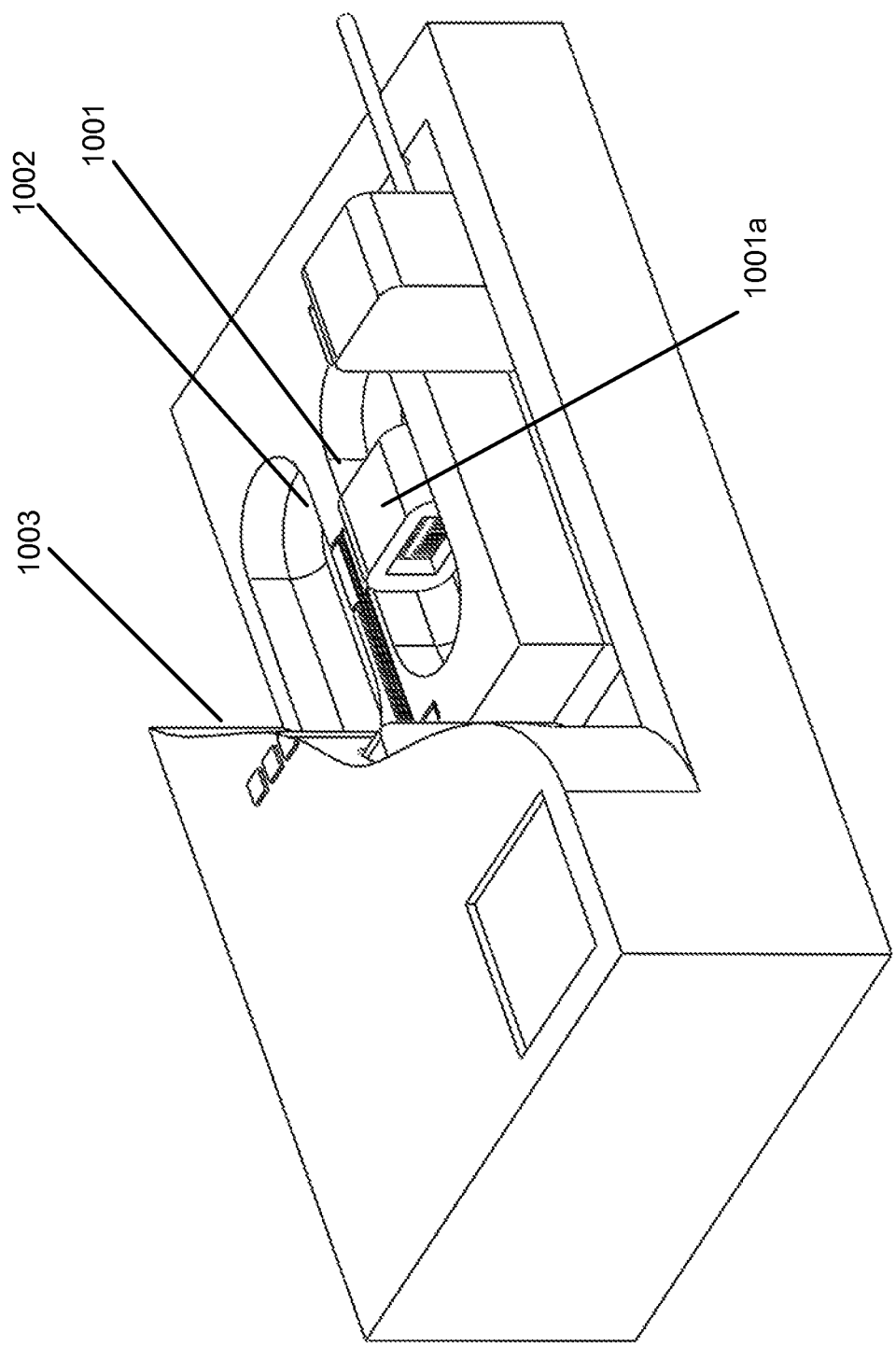
FIG. 10 is an example of a side, cut-away view of the microfluidic cartridge, including a microfluidic actuator and electrodes, according to one embodiment of the invention.

In FIG. 10, a first microfluidic actuator 1001 is shown and includes a perforated structure 1001a with fluidic passageways having at least one cross-sectional within three orders of magnitude of the characteristic thickness of the electric double layer and at least one electrode on each side of the perforated structure. The electrodes are electrically connected to metal contacts and are situated on either side of the microfluidic actuator 1001. An electric field is applied across the electrodes. In one embodiment, an electric field is applied across the electrodes through traces or wires 1002 running through or along a portion of the microfluidic cartridge and terminating at contacts 1003.

In other embodiments, the microfluidic actuator 1001 is coupled to a pulse generator or other controlled time-varying voltage source and at least one pair of electrodes. The pulse generator or controlled time-varying voltage source can produce a pattern of voltage pulses or staggered voltage pulses to the microfluidic actuator 1001.

In some embodiments, the electroosmotic flow is generated within a plurality of slit capillaries within the microfluidic actuator 1001. The electroosmotic flow can also be generated within a bed of packed beads, within a monolithic porous structure, or within an array of cylindrical channels in the microfluidic actuator 1001.

In other embodiments, the microfluidic actuator 1001 is filled with an actuator fluid with chemical properties conducive to formation at the fluid-solid interface of an electric double layer with a high effective zeta potential (e.g. an aqueous solution for a perforated structure with internal perforation surfaces containing predominantly oxygen and silicon). Application of an electric field generates electroosmotic flow within the perforations of the microfluidic actuator 1001. For a perforated structure of insulated silicon with slit-like perforations with the smaller cross-sectional dimension between 1 and 10 microns, such electroosmotic flow can drive the fluid into the passageway 101 through fluidic resistances and/or against pressure heads of 10 kPa or greater. The pressure associated with electroosmotic flow can develop within microseconds, with the primary fundamental limitation being the rate of momentum diffusion from the wall of each slit-like perforation to the center plane of each perforation.

In one embodiment, the microfluidic actuator 1001 has a fluid power generation capacity of at least $10^{-8}$ watts, is capable of sustaining power for at least 30 seconds, and has a response time for power generation of less than 10 seconds, less than 2 seconds, less than 0.2 seconds, or less than 0.04 seconds, for example. The microfluidic actuator is also capable of pressurizing at least 10 microliters of liquid, such that the liquid flows through a fluidic resistance associated with a pressure drop of at least 1 kPa at a flow rate of at least 0.1 mL per minute.

The microfluidic actuators in the invention are distinguished by being small enough to fit into a cartridge of the prescribed size, by drawing comparatively little power, and by a fast response time. Each microfluidic actuator can be cycled on and off (or transition between different fluidic power generating states) at 0.1 hertz or faster, and preferably at 1 hertz or faster, and more preferably at 10 hertz or faster. Equivalently, the microfluidic actuators have a rise time of 10 seconds or less, or a rise time of 1 second or less, or a rise time of 0.1 second or less.

A fast response time and high power are important because the reaction rate for two species initially contained within separate fluid phases is markedly faster when the two fluid phases are introduced into a reaction channel in short, discrete plugs compared to when the two fluids are introduced into a reaction channel continuously or in long plugs, or when the two fluids are introduced into a well instead of a channel (i.e., a vessel with interior dimension aspect ratios of approximate unity as opposed to a fluid container with one dimension much greater than the other two dimensions, as in a pipe or enclosed channel).

Figure 11:
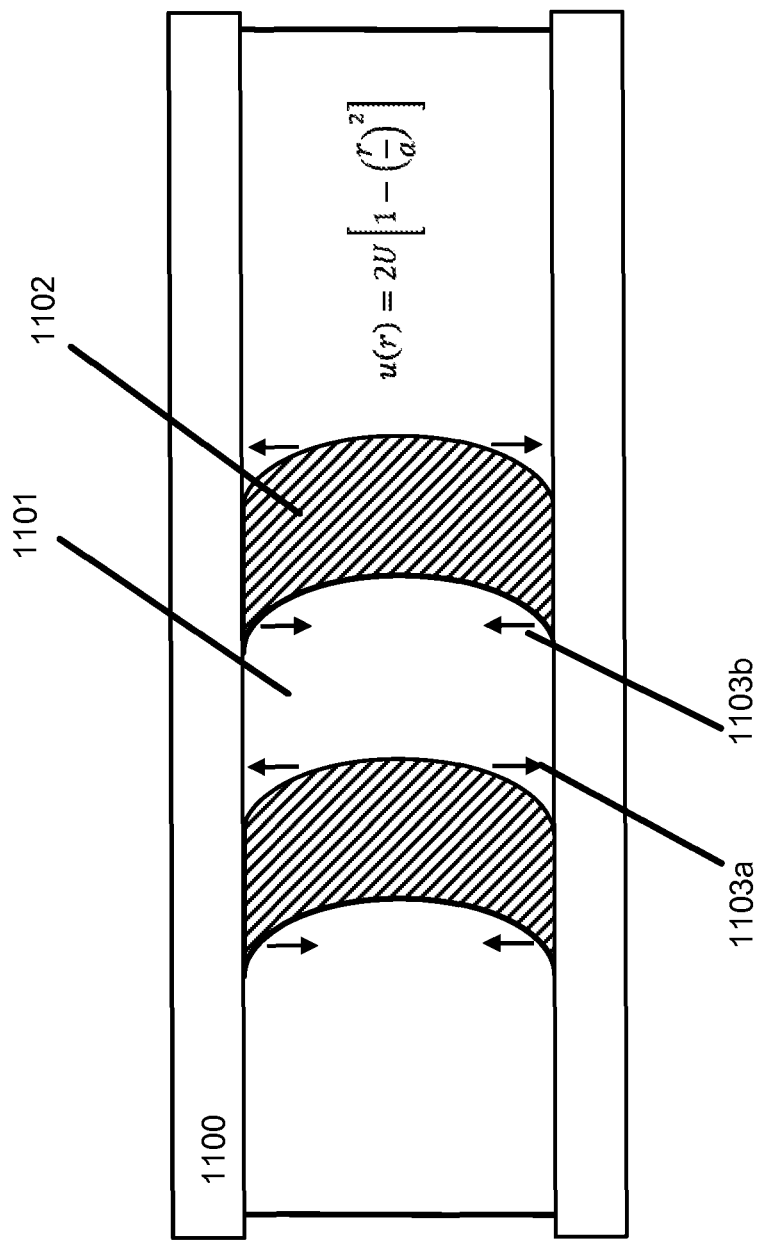
FIG. 11 is an example of fluidic plugs in the interior channel of the microfluidic cartridge, according to one embodiment of the invention.

Referring now to FIG. 11, a diagram is shown of the interior of a passageway in the microfluidic cartridge 100. Spatial non-uniformity can facilitate reaction of two fluid phases through sequential injection of alternating plugs of the fluids followed by pressure-driven flow of the train of plugs through a fluid passageway 1100. Fluid flows in the low Reynolds number regime can be well modeled by assuming the flow velocity at the fluid passageway 1100 wall to be zero (the no-slip boundary condition). For a cylindrical passageway, the radial flow velocity profile is parabolic, described by the equation:

$$u(r) = 2U\left[1 - \left(\frac{r}{a}\right)^2\right]$$

where U is the average velocity, r is the radial coordinate, and a is the radius of the cylindrical passageway. As the plugs move down the fluid passageway, the parabolic flow profile causes corresponding plug distortion 1101, 1102. Particles contained with the plugs can diffuse radially from the distorted plugs 1103. The particles diffuse radially outward 1103a from the plug fronts near the fluid passageway centerline and radially inward 1103b from the plug tails near the walls. This phenomenon is known as Taylor dispersion, which generates efficient mixing of two or more fluids. Similar diffusion effects can arise in non-cylindrical fluid passageways.

Figure 12:
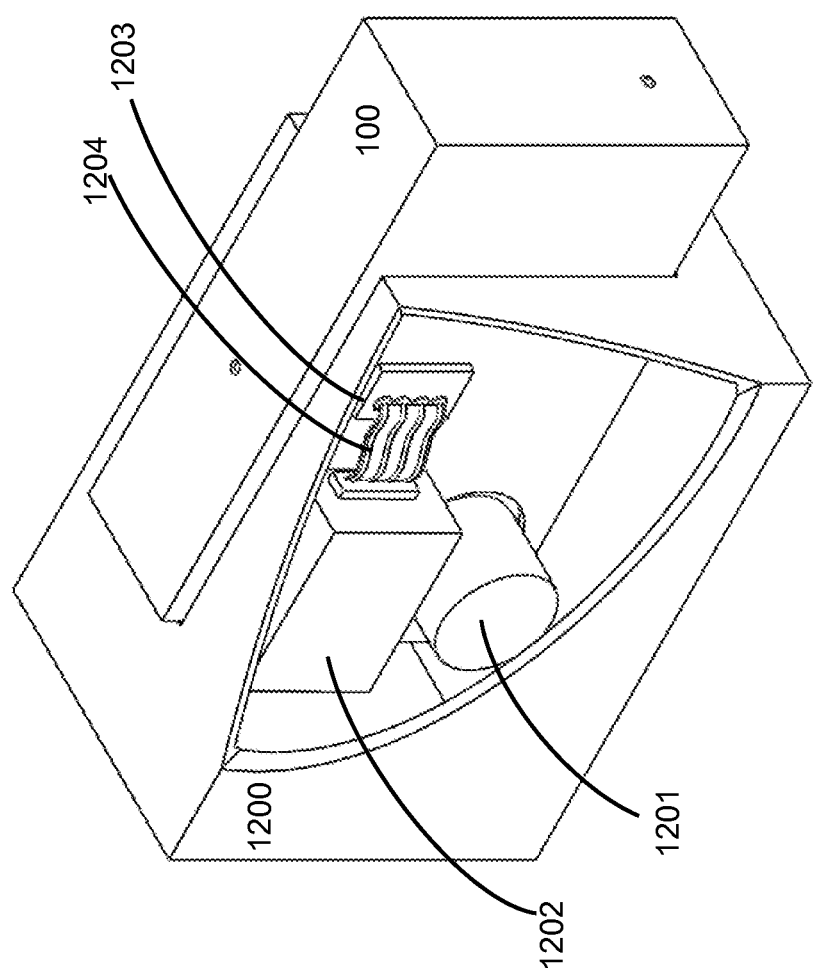
FIG. 12 is an example of an instrument that docks to the microfluidic cartridge, according to one embodiment of the invention.

In FIG. 12, the microfluidic cartridge 100 is shown docking to an instrument 1200 useful for facilitating enhanced fluid processing, for monitoring the processing, for analyzing the output of the process, or for other processing steps. The microfluidic cartridge 100 can include a sensor that senses visible light or another type of electromagnetic radiation generated within the cartridge. In one embodiment, the instrument 1200 includes an optical detector, such as a CCD imager or photomultiplier tube, or other sensor 1201. In another embodiment, the microfluidic cartridge 100 includes a detector for detecting fluorescent emissions from fluorescently-labeled molecules.

In one embodiment, the instrument 1200 contains a power supply and electrical circuitry 1202 for supplying a time-varying voltage or other input to the microfluidic actuator 1001. In another embodiment, the controlling voltage is supplied through a pin-based interconnect 1203 connected to the power supply/controller by a ribbon cable 1204. In some embodiments, the power supply is a battery.

In other embodiments, the microfluidic cartridge 100 is coupled to an external power source. The external power source can be coupled to the microfluidic cartridge 100 by an electrical connection. The microfluidic cartridge 100 can include a controller capable of controlling power delivery from the power source. The power source can be operatively coupled to the microfluidic actuator 1001. In some embodiments, the power source is electrical, pneumatic, or is a battery. The battery can be located inside the external device or coupled to the microfluidic cartridge 100 by an electrical connection.

In some embodiments, the cartridge components are produced from specialized polystyrene and/or ABS plastic resins by injection molding. Cartridge component joining can be by die-cut pressure-sensitive adhesives by thermal bonding, by ultrasonic welding, by laser welding, by epoxies, by a combination of these means, or by other means.

Figure 13:
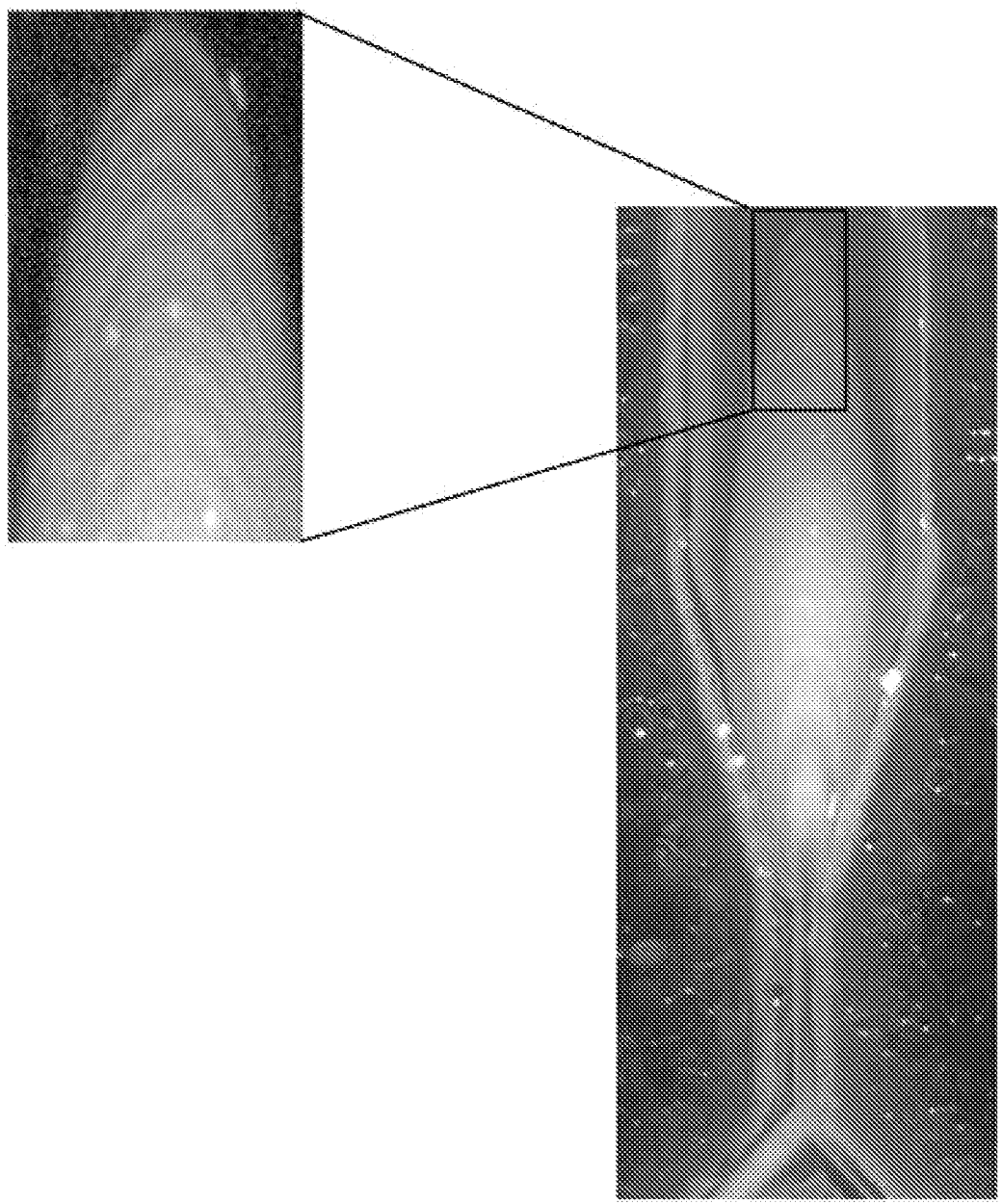
FIG. 13 illustrates an example of the fluidic plugs generated in the fluid passageways of the microfluidic cartridge, according to one embodiment of the invention.

FIG. 13 is an example of the alternating fluidic plugs generated in the fluidic passageways of the microfluidic cartridge, according to one embodiment of the invention.

Figure 14:
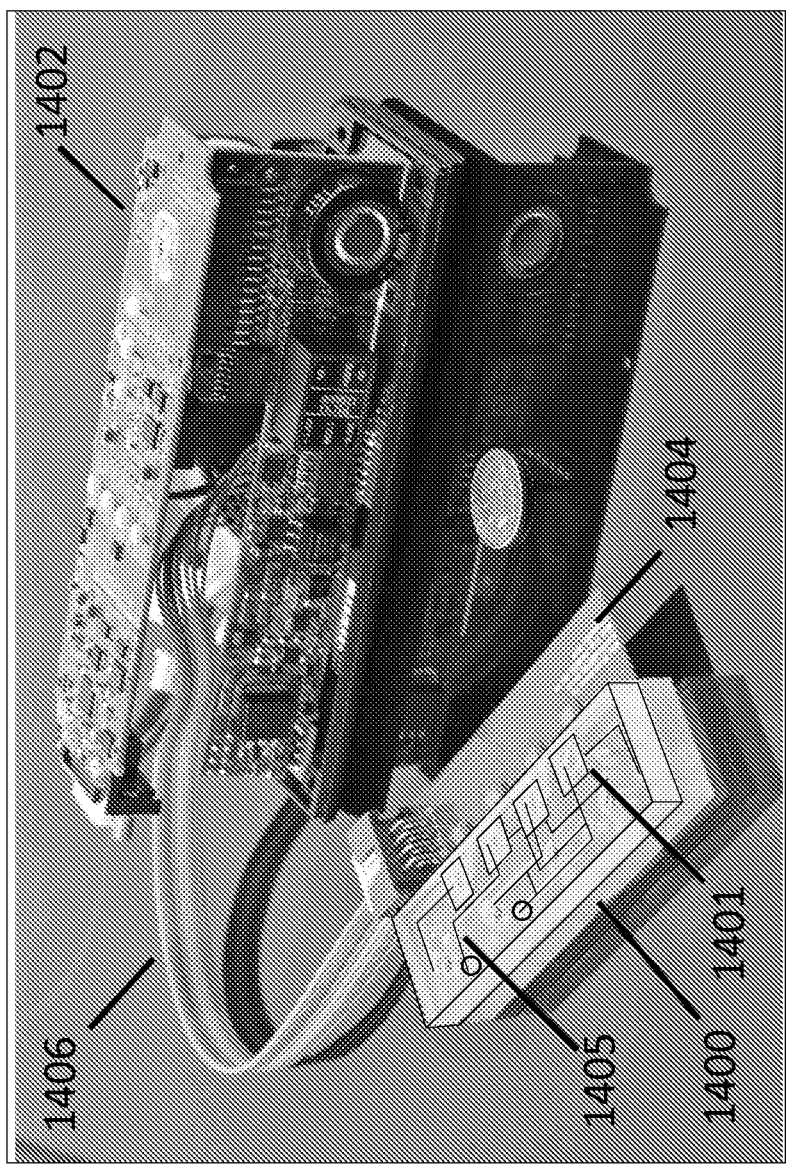
FIG. 14 is a photograph of a microfluidic cartridge and an instrument for enhanced microfluidic processing, according to an embodiment of the invention.

FIG. 14 shows an example microfluidic cartridge 1400 and an instrument 1401 for enhanced microfluidic processing, according to an embodiment of the invention. The external housing of the instrument 1401 has been removed to show the internal configuration. The microfluidic cartridge 1400 includes a microfluidic actuator 1401 (four actuators are outlined in black within the cartridge). FIG. 14 shows four microfluidic actuators 1401 inside the cartridge 1400. A network of microchannels 1405 is formed in the plastic material of the cartridge 1400. The network of microchannels 1405 includes channels connecting to each of the two fluid ports of the microfluidic actuator 1401 and to each of the two fluid ports of the other three microfluidic actuators. A circuit board 1404 includes electrical contacts for each of the microfluidic actuator electrodes. The electrical contacts are routed to the instrument 1401 through a cable 1406 with interconnects. The instrument 1401 includes a microprocessor, power management hardware, and other components for controlling the voltages applied across the actuator's 1401 electrode pair and across the electrode pairs of the other three actuators. The functionality of the instrument includes sourcing independently controlled electrical potentials of 100 volts, 200 volts, 400 volts, or other voltages, such electrical potentials being switchable under microprocessor control at frequencies of greater than 10 Hz.

Figure 15:
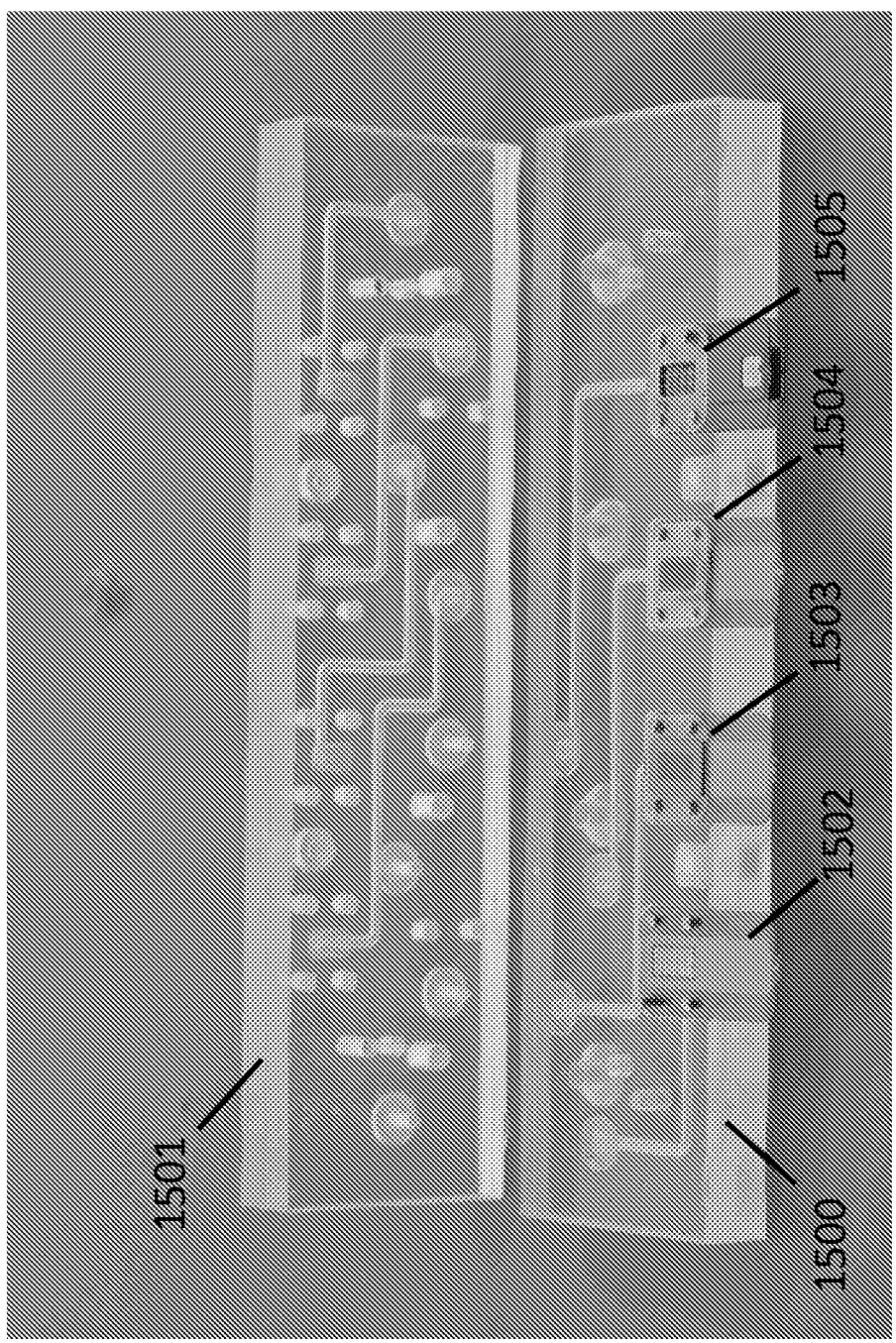
FIG. 15 is a photograph of a microfluidic cartridge for enhanced microfluidic processing, according to an embodiment of the invention.

FIG. 15 shows a microfluidic cartridge 1400 for enhanced microfluidic processing, according to an embodiment of the invention. A bottom plate 1500 and a top plate 1501 of the cartridge are shown separately from one another in this figure to show the internal configuration. When the two plates are fitted together, they form a microfluidic cartridge 1400, similar to one shown in FIG. 14. The cartridge is configured for four high-performance microfluidic actuators, which are each in a different stage of assembly in this photograph. The cartridge 1400 includes a bottom electrode 1502 and a semiconductor chip 1503 with a slat structure for generating electroosmotic flow positioned atop a bottom electrode, with an intervening chip-sealing gasket. Another semiconductor chip 1504 is similar to 1503 with an additional gasket placed on top of the slat structure semiconductor chip. The cartridge 1400 also includes an upper electrode 1505 with an additional gasket.

Figure 16:
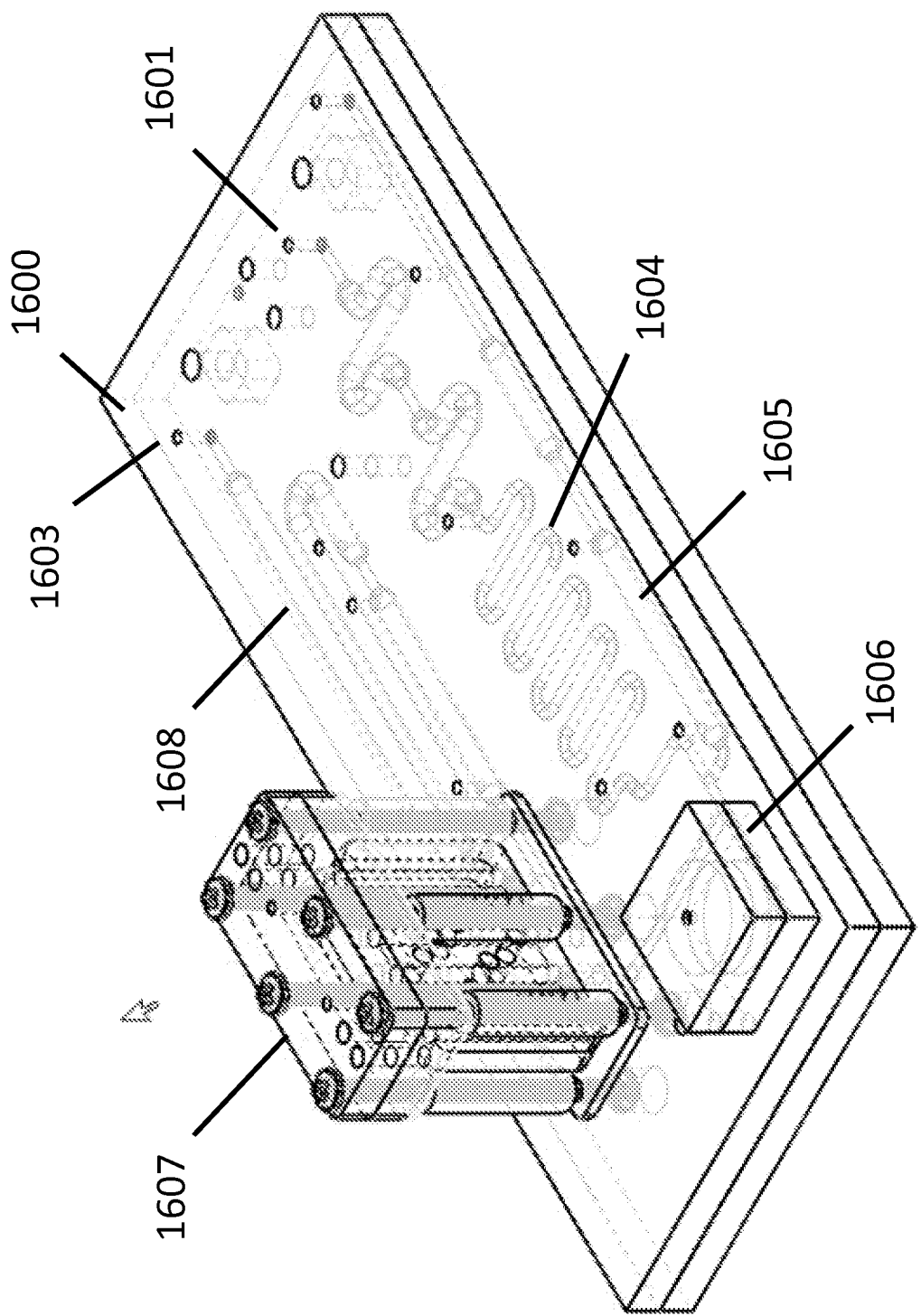
FIG. 16 is an isometric view of an exemplary microfluidic cartridge for carrying out processing steps on a sample, according to an embodiment of the invention.

FIG. 16 is an isometric view (mechanical drawing) of an example microfluidic cartridge 1600 for carrying out processing steps on a sample, according to an embodiment of the invention. The cartridge 1600 includes inlet ports 1601 and 1602, which can fluidically interface with a module containing at least one high-performance fluidic actuator. Fluid passageways 1604 and 1605 can each hold a volume of a fluid. In one example, one of the fluids can be butanol or another precipitating agent. In another example, one of the fluids can contain complexes susceptible to precipitation, such as polysaccharide-bound nucleic acids. The internal geometries of the fluid passageways 1604 and 1605 can be engineered such that prescribed fluids will exhibit prescribed flow characteristics within the passageways. For example, a fluid passageway carrying butanol can be configured with smaller cross-sectional dimensions (compared to a fluid passageway for holding an aqueous solution) to better maintain the integrity of a butanol flow front during transport driven by a microfluidic actuator. The cartridge 1600 can include chambers for receiving a reactant. The cartridge 1600 can be made of a cyclic olefin polymer or other polymer. The cartridge 1600 can comprise elements formed from more than one material such that a cartridge region intended to store a solvent resists degradation over time and to achieve other design goals. The cartridge 1600 can include a chamber 1606 into which two solutions are transported, through the action of one or more microfluidic actuators, at least one of which is a high performance microfluidic actuator. The chamber 1606 can be configured such that buoyancy effects associated with different densities of two solutions or phases to facilitate mixing of the two solutions or phases. The two solutions can be a solvent and a nucleic acid-containing solution. The mixing of the solvent and the nucleic acid-containing solution can entail transporting the fluids into the chamber 1606 where surface tension effects, buoyancy effects, or a combination of these effects causes air bubbles to be retained within such chamber upon withdrawal of the liquid phase or phases from the chamber. The cartridge 1600 includes a component 1607 incorporating a porous structure. A nucleic acid-containing solution or other solution, for example, can be passed through the porous structure. This passage can be followed by flowing of a solvent such as ethanol through the porous structure to wash away unbound material, such as proteins. Nucleic acids can be eluted into a channel 1608 by passing water through the porous structure.

Figure 17:
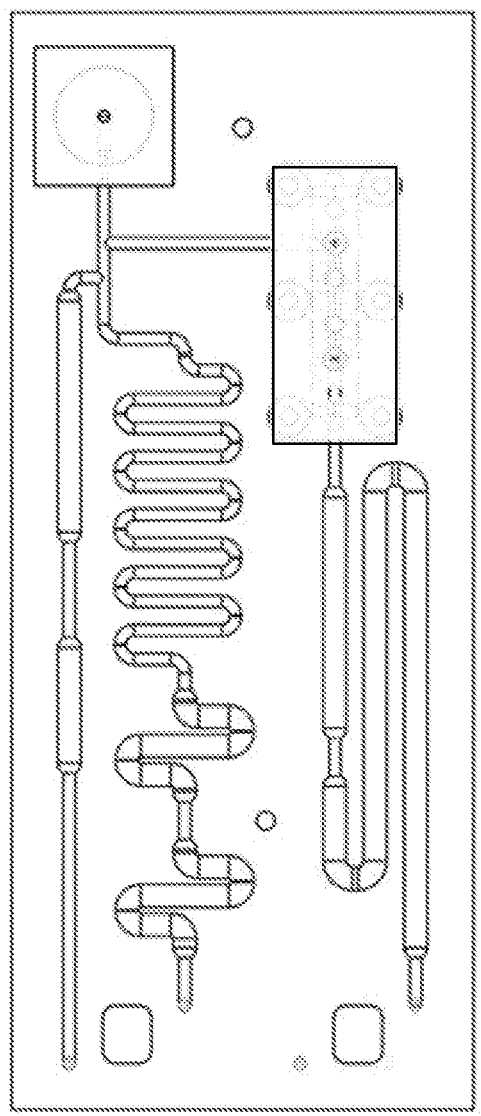
FIG. 17 is top view of a microfluidic cartridge, according to an embodiment of the invention.

FIG. 17 is top view of an example microfluidic cartridge, according to an embodiment of the invention.

Figure 18:
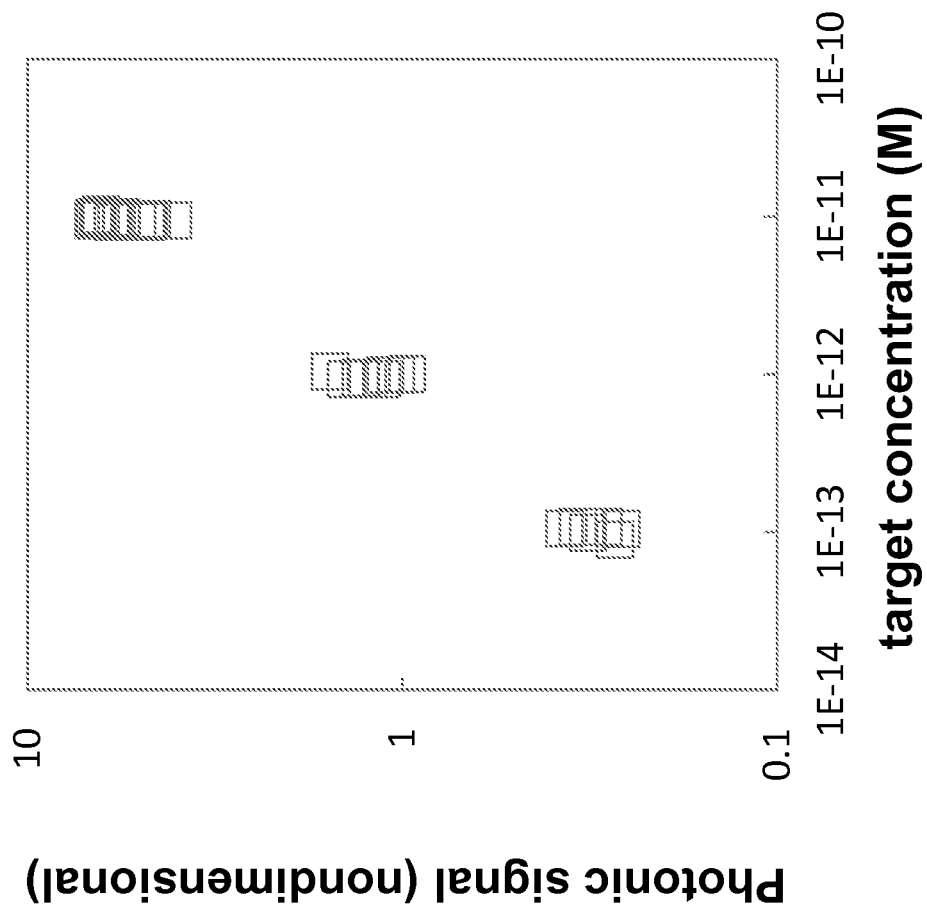
FIG. 18 shows that the high uniformity of the microfluidic cartridge for use in biochemical processes under identical prescribed conditions at different times, according to an embodiment of the invention. A series of bead-binding experiments were conducted with an oligonucleotide target present in the starting solution at concentrations of $1\times10^{-13}$ M, $1\times10^{-12}$ M, and $1\times10^{-11}$ M. Under the control of a high performance actuator, the target-containing solution was mixed with a solution containing two types of beads, and fluorescence was measured at approximately 610 nanometers, with singlet oxygen as an intermediary, such that the emitted light persists after extinguishing of the excitation source. The plotted values are indications of the starting concentration of target. At least ten assays were carried out at each concentration.

FIG. 18 shows data from experiments performed using the microfluidic cartridge or the invention. The data demonstrate that biochemical processes and other processes with high uniformity in the outcomes of multiple processes run under identical prescribed conditions at different times. A series of experiments were conducted with an oligonucleotide target present in the starting solution at concentrations of $1\times10^{-13}$ M, $1\times10^{-12}$ M, and $1\times10^{-11}$ M. Under the control of a high performance actuator, the target-containing solution was mixed with a solution containing two types of beads. The two types of beads were functionalized with two types of probes, such that each oligonucleotide target would tend to bind one of each bead. The beads were dyed such that excitation by light at approximately 680 nanometers would result in emission at approximately 610 nanometers, with singlet oxygen as an intermediary, such that the emitted light persists after extinguishing of the excitation source. The plotted values are indications of the starting concentration of target. At least ten assays were carried out at each concentration. The data has been jittered for clarity.

Figure 19:
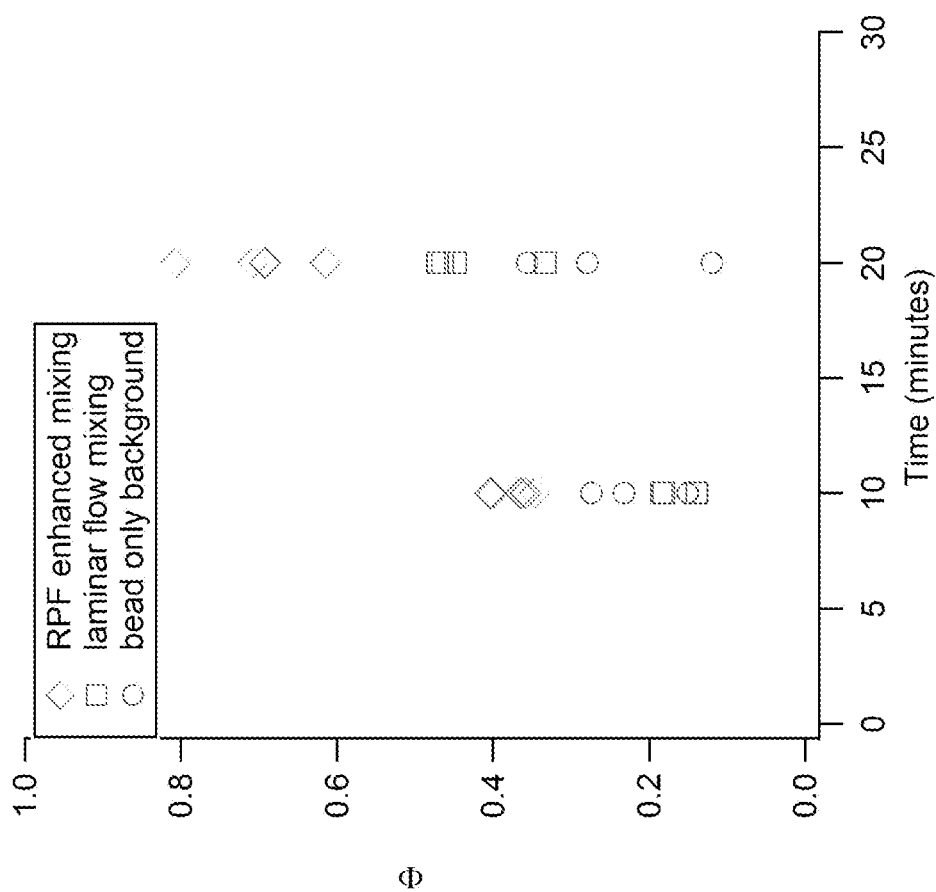
FIG. 19 shows that the amount of time required for a biochemical reaction to reach a desired endpoint, using a microfluidic cartridge of the invention. An assay similar to that described for FIG. 18 was performed.

FIG. 19 shows data from experiments performed using the microfluidic cartridge or the invention. The data demonstrate that the microfluidic cartridge can be used to shorten the time required for a biochemical reaction or other process to reach a desired endpoint, such as a signal crossing a minimum threshold value. An assay similar to that described for FIG. 18 was performed. The target-containing solution and the bead-containing solution were mixed at a junction with the flows driven by high-performance microfluidic actuators. Assays were run under two conditions: 1) with rapid pulsatile flow of the fluids while the fluids combined in the junction, and 2) with continuous flow while the fluids combined at the junction. The combined solutions were then incubated for 10 or 20 minutes and then read. As a control, assays were also run with no target in the target solution. As shown in FIG. 19, the luminescent signals (being approximately proportional to the number of bead pair-target complexes formed) for a 10 minute incubation with rapid pulsatile flow are comparable to signal for a 20 minute incubation with laminar flow.

Figure 20:
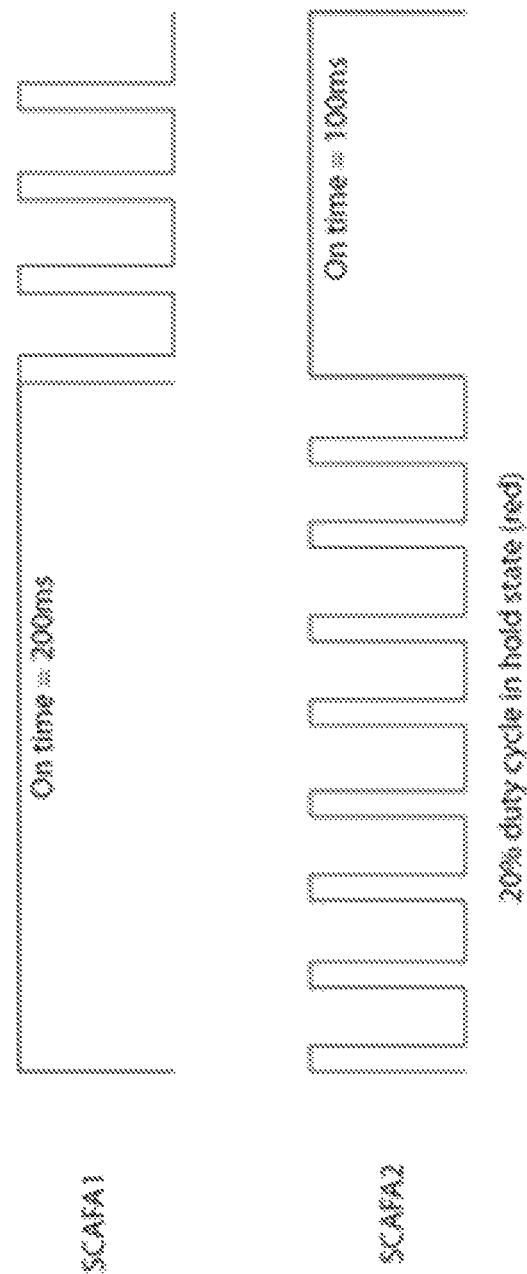
FIG. 20 is an example of electrical potential waveforms applied to pairs of high-performance actuators to achieve rapid pulsatile flow at a microfluidic junction, according to an embodiment of the invention.

FIG. 20 is an example of electrical potential waveforms applied to pairs of high-performance actuators to achieve rapid pulsatile flow at a microfluidic junction.

Figure 21:
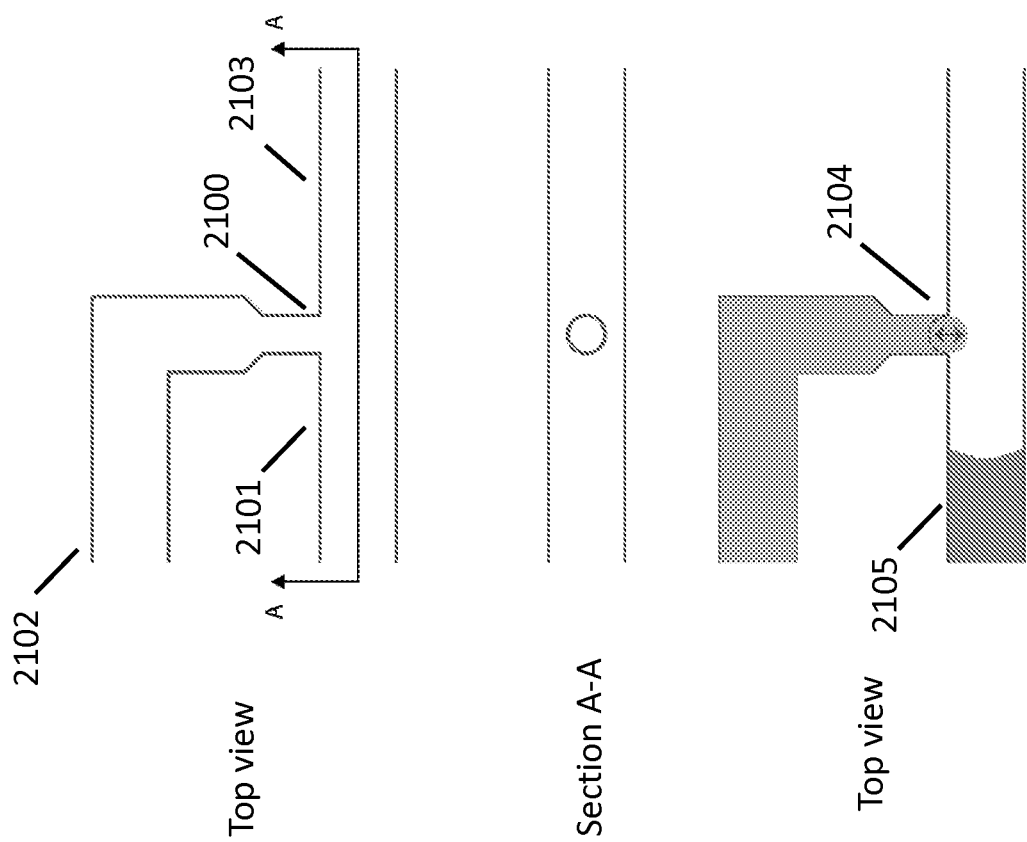
FIG. 21 illustrates an example junction geometry for synchronizing mixing of fluids, according to an embodiment of the invention.

FIG. 21 illustrates a junction geometry for synchronizing mixing of fluids using the invention. Coming into the junction 2100 is a first flow passageway 2101 and a second flow passageway 2102. The cross-sectional extent of the second flow passageway 2102 in immediate proximity to the junction is smaller than the cross-sectional of the first flow passageway 2101. The first flow passageway 2101 transitions through the junction and into the third flow passageway 2103 along an approximately straight line. The second flow passageway 2102 forms an angle with both the first and third flow passageways 2101, 2103. The reduction in cross-section of the second flow passageway 2102 in immediate proximity to the junction causes a hydrophobic solution to tend to form a meniscus at the junction. Under pulsatile flow driven by a high-performance actuator, the flow front 2104 in the secondary flow passageway 2102 can be retained at the junction, with alternating convex and concave meniscus formation, notwithstanding the application of net positive fluid power to the fluid volume by the actuator. This stalling effect can be maintained until an advancing flow front 2005 from the first flow passageway 2101 reaches the junction and contact occurs between the two flow fronts. This effect, and similar such effects, can be used to synchronize mixing fluids. Synchronized fluid mixing can be associated with better run-to-run reproducibility and other favorable assay performance characteristics.

Figure 22:
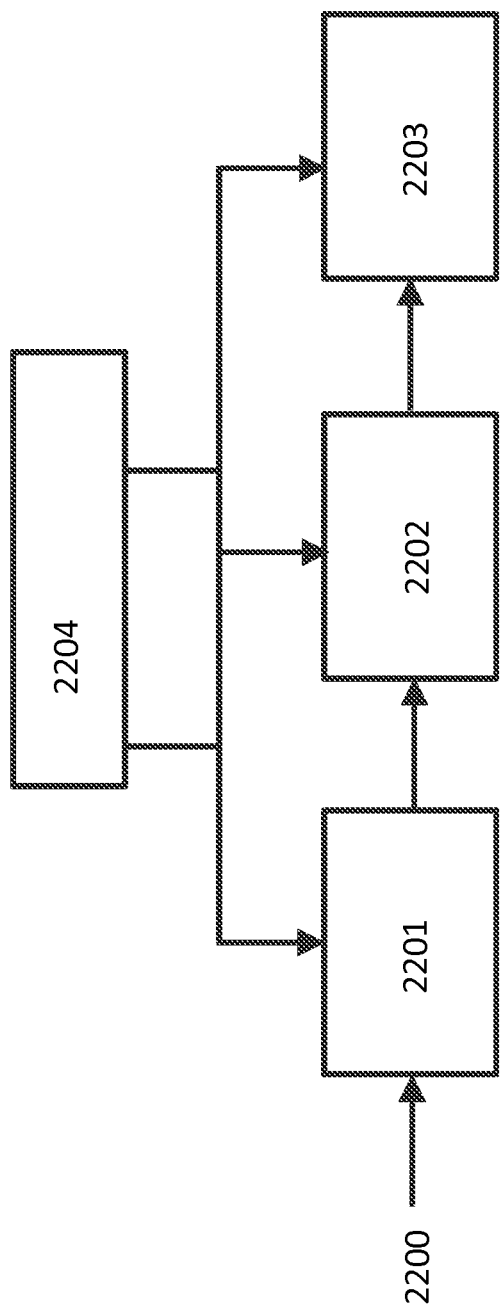
FIG. 22 is a process flow diagram for a quantitative real-time polymerase chain reaction assay using a microfluidic cartridge of the invention for applications such as quantitation of HIV genetic material, according to an embodiment of the invention.

FIG. 22 is a process flow diagram for a quantitative real-time polymerase chain reaction assay using the invention for applications such as quantitation of HIV genetic material. A sample 2200 which may contain genetic material of interest, such as bacterial DNA or messenger RNA, or viral RNA, is introduced into a processing system, which includes microfluidic channels and at least two fluidic actuators 2204, of which at least one is a high performance fluidic actuator. The fluidic actuators facilitate a polymerase chain reaction involving said genetic material in the sample in a polymerase chain reaction module 2203. The polymerase chain reaction process can be preceded by reverse transcription process in a reverse transcription module 2203. The fluidic actuators facilitate reverse transcription of RNA contained within the sample in the reverse transcription module 2202. Such reverse transcription may be preceded by a sample preparation process in a sample preparation module 2201. Such sample preparation process can be facilitated by the action of at least one high performance microfluidic actuator.

Figure 23:
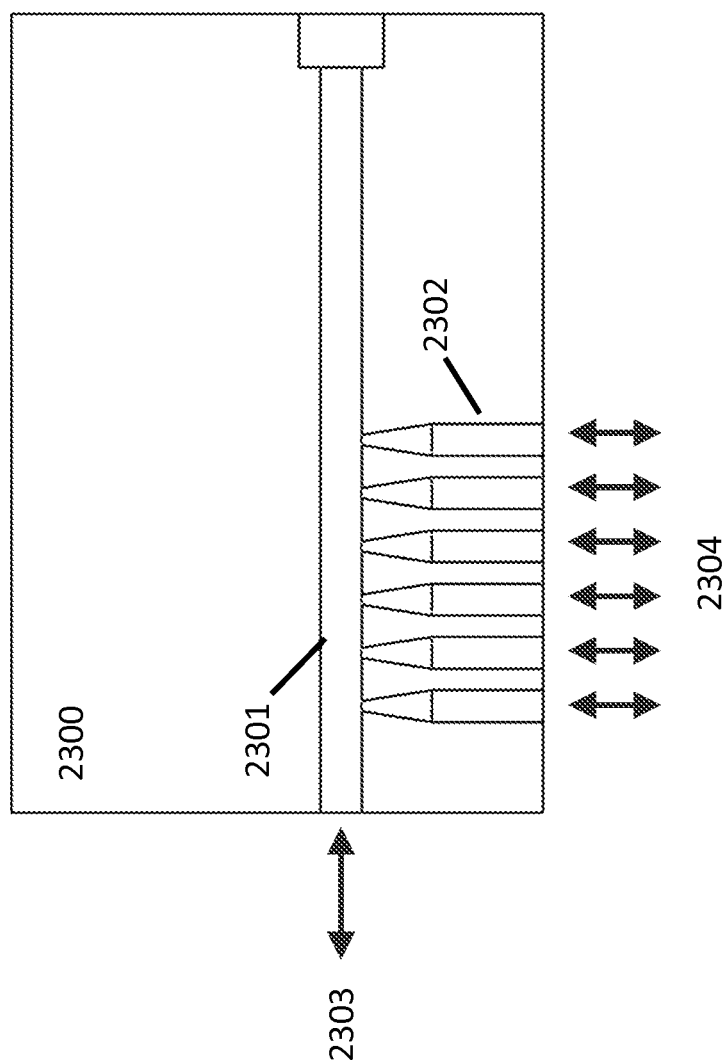
FIG. 23 depicts an exemplary architecture for using a microfluidic cartridge of the invention in the processing of partitions of fluids, where each partition, or set of partitions, can undergo a process selected for that partition or set of partitions, according to an embodiment of the invention.

FIG. 23 depicts an architecture for using the microfluidic cartridge of the invention in the processing of partitions of fluids, where each partition, or set of partitions, can undergo a process selected for that partition or set of partitions. A cartridge or other fluidic network 2300 contains a primary channel 2301. Fluidically connecting to the primary channel is an array 2302 of at least two side channels. The side channels comprising the side channel array are fluidically connected to at least one microfluidic actuator 2304. The primary channel is fluidically connected to a microfluidic actuator 2303. At least one of the microfluidic actuators 2303 and 2304 is a high performance microfluidic actuator.

Figure 24:
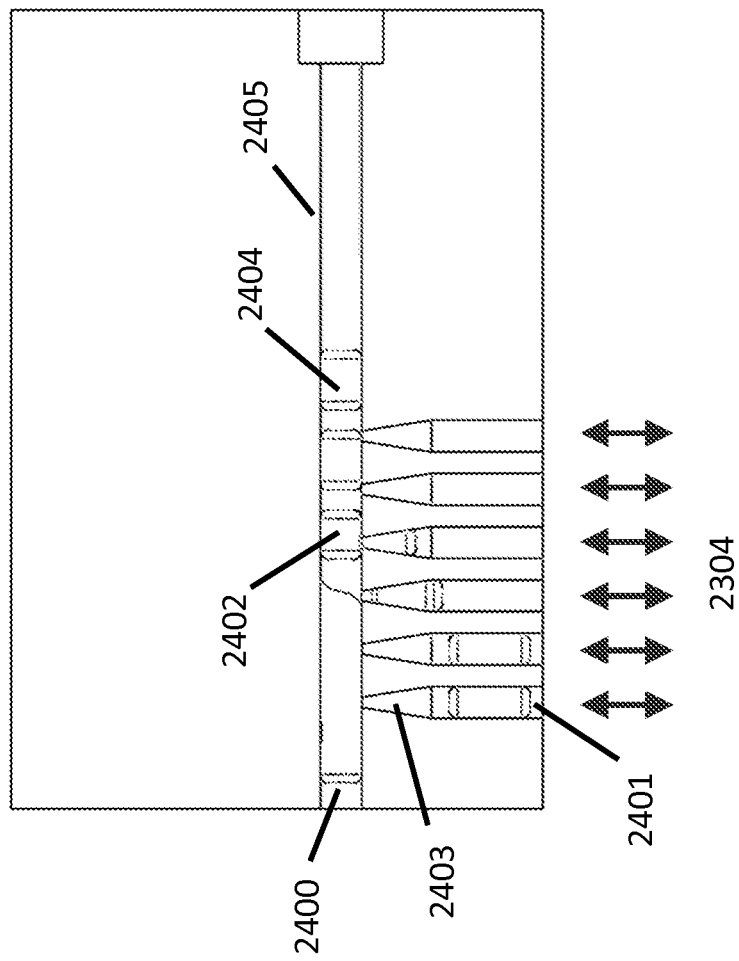
FIG. 24 depicts discrete processing of fluid partitions or sets of partitions using the microfluidic cartridge, according to an embodiment of the invention.

FIG. 24 depicts discrete processing of fluid partitions or sets of partitions using the microfluidic cartridge of the invention. A volume of a first fluid 2400 contained within a channel 2301 can be pressurized and transported through the action of a microfluidic actuator 2303. A volume of a second fluid 2401 in a side channel within a side channel array 2302 can be pressurized and transported through the action of the microfluidic actuator 2304. Additional side channels within the side channel array can be pressurized by microfluidic actuators and other means to inject volumes of fluids in side channels into the volume of fluid in the first channel at a junction 2402. Volumes of immiscible fluids or air or other gases 2403 can be injected to cause the fluid in the primary channel to be partitioned, such partitions corresponding to particular side channels, such that the fluid in a specific fluid partition predominantly comprises the first fluid combined with a prescribed second fluid injected from a specific side channel. Such mixtures of the first fluid and prescribed second fluid can proceed in a downstream channel, chamber, or other fluidic vessel 2405.

In some embodiments, the microfluidic cartridge of the invention comprises an inlet for a purified sample to be added via pipette (sample prep can be integrated as needed); integrated charged slit actuators to drive the assay processes; an amplification module in which the sample first reconstitutes PCR primers and then is cycled through three different temperature zones for reverse transcriptase step and amplification; droplet module that generates a train of droplets, each containing different beacons; a melting temperature scanning zone where reassortant resolution takes place with the main actuator shuttling the droplets back and forth past the detection zone while a unique optochemical thermal sensing method is used to precisely determine the temperature each droplet at each point during the ramp.

Figure 25:
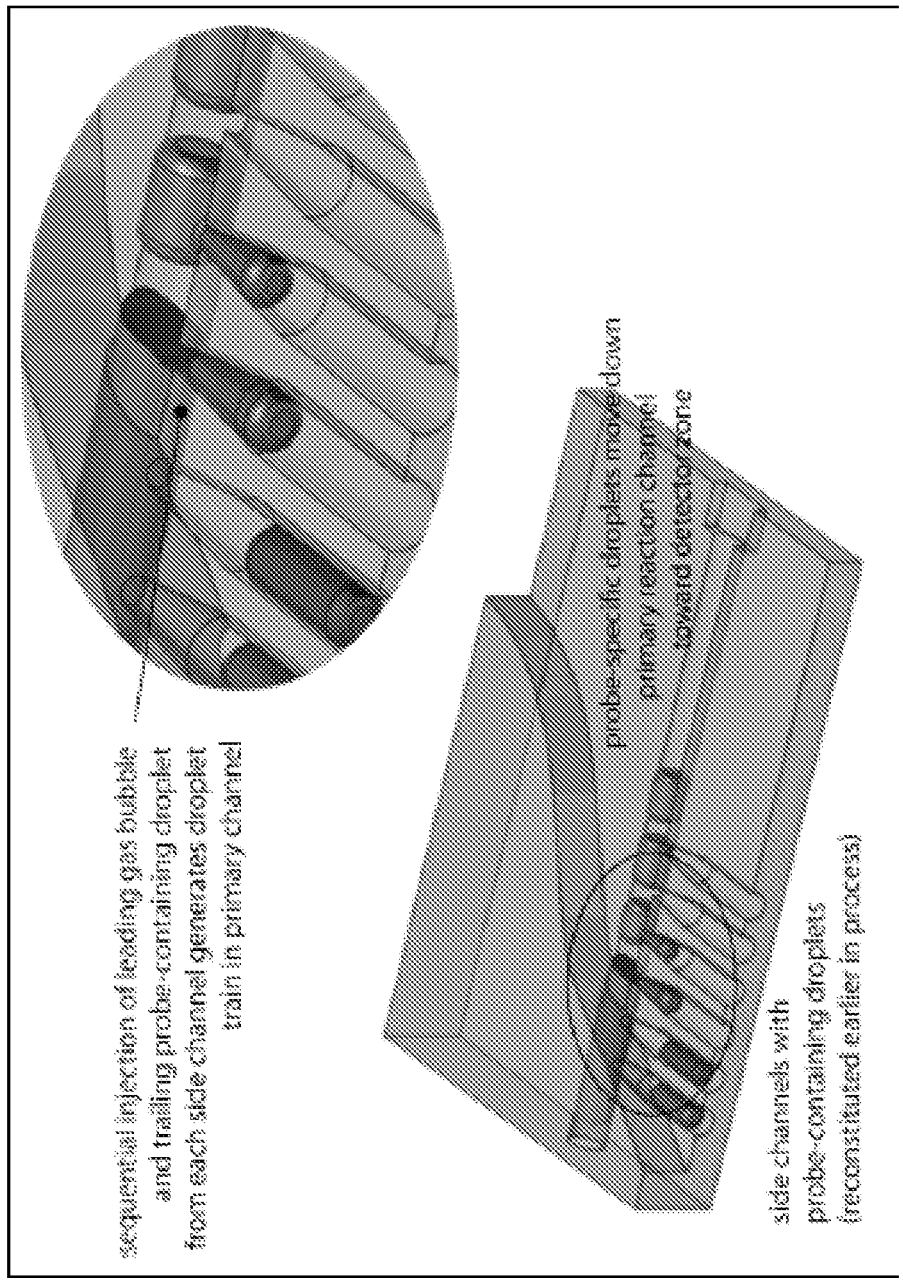
FIG. 25 shows an example of discrete processing of fluid partitions or sets of partitions using the microfluidic cartridge, according to an embodiment of the invention.

FIG. 25 shows an example of a droplet design in a microfluidic cartridge using discrete processing of fluid partitions, according to an embodiment of the invention. Various side channels under control of individual microfluidic actuators (e.g., an array of 24 charged-slit actuators) can sequentially inject a solution comprising lyophilized beacon probes into an amplicon solution (output from an amplification module) to generate a droplet train, which moves down the primary reaction channel or fluid passageway toward a detection region (such as a melt temperature analysis zone or fluorescent detector). In some embodiments, a rapid pulsatile flow driven by the individual charged slit microactuators can be used to accelerate probe binding to a large, slow-diffusing target amplicon. In one embodiment, the charged-slit actuators used for droplet generation operate briefly and serially. One high-voltage signal will be applied to the cartridge for the droplet-generation charged-slit actuators, and will be routed to the appropriate actuator by an on-cartridge high voltage de-multiplexing on the cartridge printed circuit board.

METHODS OF THE INVENTION

A microfluidic cartridge can be produced from individual plastic components and discrete microfluidic actuators. The components can be assembled by various means.

Description of generating microfluidic actuators is described in U.S. Provisional Application No. 61/771,694, filed on Mar. 1, 2013, which is hereby incorporated in its entirety by reference.

A. Introduction and Transport of Reactants, Including Starting Material

In some embodiments, a reactant or a solution containing a reactant is added to the microfluidic cartridge for processing and subsequent analysis. The reactant may include blood, sputum, tissue, bodily fluids, cells, cellular components, extracellular fluids, proteins, DNA, RNA etc. The starting material may also include dry reagents or biological materials for adding to a processing fluid. The starting material can be a fluid phase, a fluid-laden matrix, or a solid phase. The starting material can include an intermediary for a pharmacological agent or a vaccine. In some instances, the starting material includes an agricultural product, soil, or an environmental sample.

The starting material is mixed with a first fluid in a passageway of the cartridge. The first fluid can be mixed with a swab or a porous matrix, which includes soil or other environmental samples bound in the swab or porous matrix.

The starting material can be processed by adding a detergent to lyse cells or cellular membranes. Detergents disrupt the cell membrane and include sodium lauryl sulfates, hexadecyltrimethylammonium bromide or other cationic or zwitterionic detergents. Examples of detergents include Triton X-100, Triton X-114, NP-40, Tween 20, Tween 80, SDS (sodium dodecyl sulfate), and CHAPS.

Enzymes may be used for lysing cells, removing cell walls, or processing cells or cellular components in a sample. Examples of enzymes include lysozyme, lysostaphin, zymolase, cellulase, mutanolysin, glycanases, proteases, or mannase.

Processing of the starting material can be performed by mixing the sample with a homogenizing solution. For example, a solution can homogenize a tissue sample or other biologically heterogeneous sample. The homogenizing solution can include N-acetyl-L-cysteine or hypertonic saline. The homogenizing solution can include a reducing agent, such as thioredoxin.

The homogenizing solution can also include a DNAse or other proteins for breaking up of DNA and cell debris. The solution can be capable of diminishing or eliminating biological activity of a living cell, tissue, or organism. The homogenizing solution can be highly basic and can include sodium hydroxide or sodium hypochlorite.

In some embodiments, the solution include glass beads, steel beads, zirconium silicate beads, zirconium oxide beads, or other solid material used for mechanical disruption of the sample material. The beads or solid material are used to disrupt cells or cellular material, in a process called bead-beating. The solution can also include glycogen or polysaccharides.

In other embodiments, the solution comprises carrier RNA for DNA extraction from the sample. Solvents such as acetone can also be used to extract cellular proteins.

In some embodiments, the starting material comprises a dendritic cell and can be mixed with a first fluid in the cartridge and pulsed to induce an element of an immune response to insult.

The starting material can be processed and then analyzed using methods described herein. In some cases, the processed starting material is combined as a fluid with other reagents or fluids in the microfluidic cartridge.

B. Labeling of Analytes

Methods are provided for labeling analytes in the processing fluid. Examples of analytes include proteins, DNA, RNA, antibodies, peptides, or other compounds produced by a host. Analytes can include DNA, RNA, antibodies, peptides or proteins produced outside the host, such as proteins released by pathogens during the course of infection.

In one embodiment, a process for labeling analytes is provided using the microfluidic cartridge. In one embodiment, microfluidic actuators pressurize pumps, which propel a processing fluid including an analyte and a fluid comprising a labeling molecule into a common fluidic passageway, and the fluids combine such that labeling takes place. In some embodiments, the microfluidic actuators generate a Taylor dispersion of alternating plugs of fluids to mix the solutions for labeling.

Exemplary labeling reagents include chemiluminescent species, such as luminal, isoluminol, acridinium esters, thioesters, sulfonamides, and phenanthridium esters, alkaline phosphatase; fluorescent species like phycoerythrin, colloidal gold or other colloidal metals; or quantum dots. Other fluorescent reagents include lanthanides or lanthanide chelates (Europium, Samarium, Terbium, Dysprosium, etc.) and can be used in a SOCLE assay, as described below.

Quantum dots are crystalline semiconductor particles whose electronic characteristics are closely related to the size and shape of the individual crystal. Generally, the smaller the size of the crystal, the larger the band gap, the greater the difference in energy between the highest valence band and the lowest conduction band becomes, therefore more energy is needed to excite the dot, and concurrently, more energy is released when the crystal returns to its resting state. For example, in fluorescent dye applications, this equates to higher frequencies of light emitted after excitation of the dot as the crystal size grows smaller, resulting in a color shift from red to blue in the light emitted. In addition to such tuning, a main advantage with quantum dots is that, because of the high level of control possible over the size of the crystals produced, it is possible to have very precise control over the conductive properties of the material.

Fluorescence, chemiluminescence and phosphorescence are three different types of luminescence properties (emission of light from a substance). Fluorescence is a property where light is absorbed and remitted within a few nanoseconds (approx. 10 ns) at a lower energy (higher wavelength), while bioluminescence is biological chemiluminescence, a property where light is generated by a chemical reaction of an enzyme on a substrate. Phosphorescence is a property of materials to absorb light and emit the energy several milliseconds or more later (due to forbidden transitions to the ground state of a triplet state, while fluorescence occurs in exited singlet states).

Fluorescent labeling is a process of covalently attaching a fluorophore to another molecule, such as a protein, nucleic acid molecule, lipid or other small molecule. A reactive derivative of a fluorophore can be used to selectively bind to a functional group in a target molecule. Common reactive groups include isothiocyanate derivatives, such as FITC and TRITC, succinimidyl esters, such as NHS-fluorescein, maleimide activated fluorophores, such as fluorescein-5-maleimide, or fluorophore-labeled oligonuclotides, such as 6-FAM phosphoramidite. Fluorescent proteins or fluorophores can also be non-specifically or non-covalently attached to proteins. The fluorescently-labeled molecule is excited by light (an excitation source) and emits fluorescence, which can be detected by the visible eye or fluorescence detectors. Various light sources may be used as excitation sources, including lasers, photodiodes, and lamps, xenon arcs and mercury-vapor lamps in particular.

The analyte can be labeled with a fluorophore for detection by FRET (Förster (Fluorescence) resonance energy transfer)), resonance energy transfer (RET) or electronic energy transfer (EET). FRET is a mechanism describing energy transfer between two chromophores. A donor chromophore, initially in its electronic excited state, may transfer energy to an acceptor chromophore through nonradiative dipole-dipole coupling. For example, an analyte that is labeled with a cyan fluorescent protein (CFP) can transfer energy after excitation to a yellow fluorescent protein (YFP), which emits fluorescent signal for detection.

Analytes can be labeled and detected using silica beads, particles, or paramagnetic beads. The beads or particles hybridize or bind to a target analyte and can be purified or separated out from the fluid by magnetic separation, affinity purification, etc.

Analytes can also be labeled and detected using oligonucleotide probes. The probe can be RNA or DNA, or modified versions thereof. The oligonucleotide probe can be designed to target a specific nucleic acid sequence, specific to a virus, bacterium, infectious organism, or human gene. Examples of target nucleic acid sequences include sequences specific to HIV, hepatitis B, hepatitis C, *M. tuberculosis, C. trachomatis*, an influenza virus, respiratory syncytial virus, a virus of the human respiratory tract, or a cancer-associated gene (e.g., ERRB2). The oligonucleotide probe can be labeled with a fluorescent molecule, a luminescent signaling molecule, or a quencher molecule.

Other examples of labeling reagents comprise a labeled carbohydrate, a labeled nucleic acid, or a labeled protein for measurement of a specific cellular compound.

In some embodiments, the fluids in the fluidic passageways comprise a dye for specific or non-specific labeling of a cell.

In other embodiments, the fluids in the fluidic passageways comprise a primer, a probe, or a combination of a primer and a probe, and an enzyme capable of catalyzing a polymerase chain reaction, a transcription-mediated amplification, a nucleic acid sequence-based amplification, or another chemical reaction for amplifying at least one specified nucleic acid sequence. The enzyme can comprise a DNA polymerase, a reverse transcriptase, an RNA polymerase, an RNAse H, a DNA helicase, or a recombinase.

In another embodiment, the labeling reagents are attached, bound or linked to a wall of a fluidic passageway.

When a fluid comprising a target analyte passes through the passageway in the cartridge, the target analyte associates or binds to the bound reagent.

Labeling an analyte can be followed by detection of the analyte or measurement of the quantity of analyte present in the sample. For example, a species that is labeled with fluorescent particles can be detected by illuminating with light at the excitation frequency of the fluorescent label and measuring the emitted light.

Labeling can also be followed by separation of the analyte. For example, one could separate analytes by labeling a species with magnetic particles and by imposing a magnetic field in which the labeled species are differentially transported.

C. Labeling Proteins with Antibodies

A sample or starting material can be combined with a first solution containing a first set of antibodies, which specifically bind a target protein in the sample, for example. The combined fluids can move by electroosmotic flow in a passageway, passing by a region of the wall of the fluid passageway. The wall is bound with a second set of antibodies that specifically bind a different epitope of the target protein. Target proteins binding to the wall region and forming a sandwich with the first set of antibodies can be detected by an spectrometer or other instrument that measures fluorescence.

By using antibodies specific to more than one target and providing more than one variety of antibody, e.g., each antibody attached to a separate region of the wall, multiple targets can be specifically detected and measured. The use of multiple fluorescent labels further extends the utility.

Many other assays similar to the basic antibody sandwich assay can be carried out, such as detecting genomic material using pairs of oligonucleotide probes. Among many suitable non-optical assay means are electrochemical assay methods and assay methods using paramagnetic beads.

D. SOCLE Detection Assay

An exemplary labeling and detection method for analytes used in a microfluidic cartridge is singlet oxygen catalyzed light emission (SOCLE). SOCLE is a variant on luminescence oxygen channeling (Ullman et al., Luminescent oxygen channeling assay (LOCI): sensitive, broadly applicable homogeneous immunoassay method. (1996). Clin. Chem 42, 1518-1526; Ullman et al., Luminescent oxygen channeling immunoassay: measurement of particle binding kinetics by chemiluminescence. (1994). Proceedings of the National Academy of Sciences 91, 5426-5430) and is widely used in well-format commercial immunoassay systems.

The bipartite SOCLE assay incorporates probe-conjugated photosensitizer and chemiluminescent/fluorescent emitter beads. Excitation of a sensitizer bead with light generates a fluorescent signal only if hybridization to a target has brought a sensitizer and an emitter bead into close proximity (<200 nm). Singlet oxygen acts as an energy-transporting intermediary. Because diffusion of the singlet oxygen between the sensitizer and emitter beads requires finite time, there is temporal separation of the excitation and photon counting steps. Background fluorescence is therefore reduced by several orders of magnitude, as the exciting radiation source is shut off prior to reading. The SOCLE assay is non-enzymatic (i.e. no thermolabile proteins).

In one example, a microfluidic cartridge includes a fluid comprising the first target nucleic acid and a second fluid comprising a sensitizer oligonucleotide conjugated to a sensitizer bead. The sensitizer oligonucleotide includes a complementary sequence to the first target nucleic acid. The first target nucleic acid molecule hybridizes with the sensitizer oligonucleotide conjugated to a bead by combining the two fluids together, using the methods described above. For instance, the two fluids are pressurized and combine by electroosmotic flow into a junction that combines the two fluids in the passageway. A third fluid can include second target nucleic acid molecule that is complementary to the first target nucleic acid molecule and also complementary to an emitter oligonucleotide conjugated to an emitter bead. The third fluid can be mixed with a fourth fluid so that the emitter oligonucleotide-bead hybridizes with the second target nucleic acid. The sensitizer-bead complexed molecules and the emitter-bead complexed molecules can be mixed ((a) first target nucleic acid and sensitizer oligonucleotide-bead complex and (b) second target nucleic acid and emitter oligonucleotide-bead complex) at another junction that combines two fluidic passageways by generating plugs of alternating fluids using the microfluidic actuators described above. The hybridization of the first and second target nucleic acids can produce a signal when the two complexes hybridize and the emitter bead and the sensitizer bead are in near proximity to each other (e.g., <200 nm apart). In some instances, the sensitizer-bead complex and the emitter-bead complex both hybridize to a bridge probe (oligonucleotide) that is complementary to the first target nucleic acid and the second target nucleic acid. The bridge probe helps to form an oligonucleotide complex between the emitter oligonucleotide-bead complex and the sensitizer oligonucleotide-bead complex.

In other example, a fluidic passageway comprises a matrix for co-localizing the sensitizer oligonucleotide-bead complexes or a matrix for co-localizing the emitter oligonucleotide-bead complexes. Fluids that comprise the target nucleic acid molecules can hybridize to the sensitizer oligonucleotide-bead or hybridize to the emitter oligonucleotide-bead complexes.

From within the cartridge, the sample may require excitation at 680 nm and detection at 615 nm. The readout from the sample may be detected from the detection window of the cartridge. The excitation steps can occur in sequence with a transition period on the order of milliseconds or less. The excitation source can be high intensity, and the detector can be highly sensitive. The optics module should be designed to satisfy these requirements. The excitation source is a light-emitting diode (LED), an efficient light source which emits over a relatively narrow range of wavelengths. Light emitted by the assay is detected by a photomultiplier tube (PMT). Lenses, bandpass filters, and a dichroic beamsplitter direct light from the LED into the cartridge and from the cartridge into the PMT.

A typical read cycle sequence entails setting the PMT control voltage low (typically 0.3V), turning on the LED for 0.5 seconds, turning the LED off, and finally increasing the PMT control (typically to 0.8V) to read the results of SOCLE signaling in the read well. Custom analog hardware was built to provide current-to-voltage conversion, filtering, and amplification or attenuation. Five analog-to-digital converter channels (three signal channels with different amplification, temperature, and PMT control voltage) are read for the time the experiment is running (typically 0.7 seconds). The data from the five channels is streamed in real time to the microprocessor, which integrates the signal and compares it to a standard curve or look-up table to determine starting sample concentration. The dynamic range over which the starting sample concentration is determined can be increased by decreasing the PMT control voltage after a saturating signal is measured.

E. Droplet-Based Assays

The microfluidic cartridge of the invention can be used for detecting and quantitating a plurality of analytes in a sample or starting material through an assay that includes dividing the sample or starting material into a plurality of partitioned assay mixtures that are isolated from one another in respective droplets by an intervening, immiscible carrier fluid. This division can take place anywhere within the cartridge and can occur at any stage of the processing of the sample or starting material. Examples of stages at which the division can occur include: immediately upon introduction of a sample or starting material into a cartridge; after a filtration process; after a nucleic acid extraction process; after a process in which a segment of genomic material in all species of a particular category (such as the 16S region for bacterial targets) is amplified by polymerase chain reaction or another method; and after labeling with a fluorescent bead or other signaling particle.

The microfluidic cartridge of the invention can include a plurality of fluidic passageways that meet at junctions in the cartridge. In some embodiments, this is a T-junction or a Y-junction. Two immiscible fluids from two separate fluidic passageways can meet at the junction in the cartridge and form droplets at the junction as the two fluids collide (e.g., oil-in-water droplets, water-in-oil droplets). The junction and fluidic passageways can be narrow enough such that one droplet is formed when two immiscible fluids meet at the junction. Multiple droplets can be formed as the fluids flow forward at the junction and are joined in a single passageway.

In some embodiments, the microfluidic cartridge of the invention can be used to precisely generate a plurality of partitioned assay mixtures, with arbitrarily chosen volumes, without fluid transport or mechanical energy transfer into the cartridge from an external component. The capability of choosing the volumes of the partitioned mixtures arbitrarily differentiates droplet formation using the invention; in contrast, with droplet formation by a droplet generator which does not include a high-performance actuator, the junction geometry and the fluid properties are primary determinants of partition volumes, limiting the capacity to arbitrarily choose these volumes. At least one microfluidic actuator can act on a processing fluid contained within a fluidic passageway, causing such fluid to travel toward a junction. Similarly, a second microfluidic actuator can act on an immiscible carrier fluid within a second fluidic passageway, causing such carrier fluid to travel toward the junction. If at least one of the actuators in the microfluidic cartridge is a high-performance actuator, the pressurization of either the first fluid or the carrier fluid, or both, can be rapidly pulsed or otherwise pressurized in a time-varying manner, such that fluid partitions with desired partition volumes are formed at the joining of the two fluids at the junction.

The microfluidic cartridge of the invention can also be used for droplet-based assays where droplet formation facilitates detection and quantitation of multiple analytes within a single starting sample, known as multiplexing. Dual plugs of immiscible carrier fluid and reagent can be sequentially injected into a plug of sample, forming a plurality of fluid partitions, the reagents chosen such that different reactions take place within certain partitions, and each such reaction corresponding to detection of a specific analyte of interest. Each reaction can take place within a single droplet and the detector in the microfluidic cartridge can detect emissions or signals from each reaction in the droplets.

In another embodiment, the microfluidic cartridge of the invention can be used to generate droplets and to perform PCR amplification in a plurality of droplets in the cartridge. In some embodiments, each droplet includes target nucleic acid molecules, enzymes, and a PCR primer mix for amplification module of nucleic acid molecules in a sample. Each droplet can comprise PCR reagents and can be cycled through three different temperature zones in the microfluidic cartridge (e.g., for reverse transcriptase reactions and amplification). In some embodiments, the microfluidic cartridge can generate droplets in one region of the cartridge (e.g., a junction of at least two fluid passageways is used to generate a train of at least 24 droplets). The PCR amplification can occur through movement of the droplets (via the microfluidic actuator) through pre-set temperature zones in the cartridge.

In further detail, amplification can be accomplished by shuttling a fluid comprising the droplets between three temperature zones in the cartridge for reverse transcription and amplification. The low thermal mass of the fluid plug allows the fluid temperature to equilibrate in each zone in a few seconds, resulting in rapid amplification cycles. The fast transient response time of the charged slit actuators further enhances the amplification process by shortening the time required to shuttle the solution between the zones. In addition to the three zones, the amplification module can include a reagent reconstitution zone. A single relatively large (e.g., 4 mm×6 mm) charged-slit microactuator can be used for executing these steps. For amplification module thermal engineering, thermal analysis can be carried out in COMSOL to establish requisite cartridge thermal mass allocation to hold zone temperatures to +/−1° C. of nominal as the solution moves between zones.

In other embodiments, the cartridge includes a melting temperature scanning zone (where reassortant resolution takes place with the main actuator shuttling the droplets back and forth past the detection zone) and an optochemical thermal sensing method is used to precisely determine the temperature of each droplet at various time points in the cartridge.

In one embodiments, a droplet generator in the cartridge (as shown in FIGS. 23-25) is positioned downstream of an amplification module. The droplet generator can execute the individual reconstitution of a number of lyophilized reagent plaques (e.g., 24 plaques containing 24 beacons) used in a melting temperature scanning assay and then generates a droplet train by sequentially pulsing each beacon solution volume into an amplicon solution. Flow in the main channel can be driven by a large charge slit actuator used in the amplification stage. In one embodiment, a number of small actuators (e.g., 24 small actuators) can each drive one side of the channel, including both dried beacon reconstitution (in hybridization buffer) and injection. The side channel actuators and main actuator can work together for shuttling the droplet train back and forth past a detector during a melt temperature analysis.

In some embodiments, the microfluidic cartridge is coupled to an instrument comprising charged-slit actuator drive electronics, cartridge temperature control, optical components for detection, instrument-control electronics, a touchscreen user interface controlled by a separate microcontroller, power electronics, and communications hardware, including RFID, WiFi, and Ethernet connectivity.

F. Mixing-Enhancing Junction Geometries

In addition to mixing fluids at a simple t-junction or y-junction, the invention can be used to mix fluids in junctions with junction geometries which specifically facilitate rapid mixing. A junction configuration where one or more channel cross-sections in immediate proximity to the junction are smaller than the cross-sections more distant from the junction—sometimes referred to as a neck-down junction—can, in combination with the invention, facilitate more rapid macroscopic mixing than with either a non-neck-down junction with the invention, or a junction (with or without neck-down) without the invention. The smaller channel cross-sections in immediate proximity correspond to smaller minimum fluid plug volumes for discrete plug injection using the invention. After the pulse train moves beyond the necked-down region of the reaction channel in immediate proximity to the junction, conservation of mass requires that small-volume fluid plugs expand into plugs that are shorter in the axial dimension compared to that within the necked-down channel region. The contribution to mixing of Taylor dispersion is correspondingly increased compared to a junction process with larger-volume plugs as in a non-neck-down geometry.

G. Channel and Junction Features for Using Surface Tension Effects to Improve Control Over Fluids in a Cartridge, Reduce Bubbles, Synchronize Fluids for Mixing at a Junction, or Otherwise Improve Assay Performance Features of the channels in proximity to the junction can be used to improve the performance of mixing using the invention. For fluids which are hydrophobic relative to the material comprising the fluid passageway, inclusion of cavity-like features in proximity to a junction can be used with the invention to align fluids prior to mixing. For a cavity feature which is an approximately uniform radial expansion and contraction of an approximately cylindrical channel, the axial length along which such expansion and contraction occurs being small compared to the channel diameter, the flow front of a fluid volume can be retained within the cavity when pressurized by a high-performance actuator acting at a given duty cycle and average power due to energy storage associated with surface tension-mediated flow front deformation at the entrance to the cavity. An increase in the duty cycle and/or average power of the high-performance actuator can overcome the meniscus energy storage effect and cause the fluid flow front to move past the cavity entrance. If the flow characteristics (such as flow rate) of a fluid within a cartridge are subject to uncertainty, for example, because of patient-to-patient variation in hematocrit for whole blood samples, the low-duty-cycle/low-power stalling effect at a cavity can be used to reduce the impact of such uncertainty on assay performance, for example, by maintaining operation of the high-performance actuator at the low-duty-cycle/low-power state until such time has elapsed that a fluid at the low-flow-rate extreme of the parameter space contemplated for cartridge design (e.g. with a hematocrit at the high end of the physiological range). Through a similar combination of effects, with the invention, a cavity can function as a trap for bubbles of air or another gas entrained in a fluid.

The invention can also be used to improve assay performance through the inclusion of cavity-like feature in the side channel of a t-junction in immediate proximity to the junction. For a cavity feature which is an approximately uniform radial expansion of an approximately cylindrical channel, the axial length along which such expansion occurs being small compared to the channel diameter, the flow front of a first fluid volume can be retained within the cavity when pressurized by a high-performance actuator acting at a given duty cycle and average power due to energy storage associated with surface tension-mediated flow front deformation at the entrance to the cavity. Provided the axial length of the cavity is small compared to the channel diameter, a second fluid passing through the approximately straight t-junction passageway can overcome the meniscus energy storage effect and cause the flow front of the first fluid to pass into the junction.

H. Reaction with Solid Phase to Facilitate Detection of Constituents

The invention can be combined with known methods to facilitate reactions between constituents of a solution and a solid phase to facilitate detection or detection and quantitation of such constituents. A solution can be flowed into a chamber containing one or more interior surface regions on which probes are bound. Such surface-bound probes may be oligonucleotide probes, antibody probes, or other probes. The surface-bound probes may be positioned relative to sensing elements or sensing systems facilitating identification of binding events between surface-bound probes and solution-phase reactants. Such reactants may be oligonucleotides, proteins, sugars, cells, or other reactants. The surface-bound probes can be configured in a one-dimensional, two-dimensional, or three-dimensional array. The sensing elements or sensing systems may be configured for measuring parameters of interest of individual elements of said array. The sensing elements may be engineered to measure parameters including temperature, pH, and electromagnetic radiation. Two microfluidic actuators, at least one of which is a high-performance actuator, can be used to induce time-varying flows in the vicinity of some or all of the probe-functionalized surface regions. The time-varying flows can result in exchange of volumes of solution in immediate proximity to such surface regions, such that fluid volumes containing comparatively large concentrations of unbound reactants are brought into proximity to said surfaces such that the reactants can bind to such surface-bound probes.

I. Metering of Reactant

The invention can draw a prescribed volume of a fluid-phase reactant such as blood, plasma, urine, or another biological fluid, or a solution containing a component for a chemical or biochemical synthesis process, into a cartridge or other microfluidic network for subsequent processing or analysis. A volume of reactant can be loaded into a chamber by pipetting, by pouring from another container, by flow directly from a source (such as blood flowing directly from an opening in the skin produced by the action of a mechanical lancet), or by another means. The loading process can be imprecise, such as a nurse or other healthcare professional visually ascertaining that the volume of reactant exceeds a minimal volume indicated by a fill line on the chamber. A first microfluidic actuator can then draw a volume of reactant into a fluid passageway, or a chamber different from the intake chamber, by operating for a prescribed period of time and at a prescribed power level, such operational parameters having been previously determined by characterization of the microactuator and the associated microfluidic network to correspond to a preferred volume for subsequent processing. This is referred to herein as open-loop metering. Alternatively, said first microfluidic actuator can draw a volume of reactant into a fluid passageway by operating until such time as a sensor indicates that the volume of reactant within said fluid passageway has reached a prescribed value. Such sensor can be a capacitive sensor that exhibits a change in capacitance when the reactant flow front advances within the channel to a predetermined position. This is referred to herein as closed-loop metering.

The volume of reactant drawn into the first fluid passageway can be mixed with other fluids at a junction, such mixing being driven by the combined action of the first and second microfluidic actuators, one of which is a high performance actuator, as described herein. The reactant drawn into the first fluid passageway can reconstitute a dried-down or lyophilized material, either immediately upon being drawn into the first passageway or chamber, or at a later stage of processing.

J. Lysing of Cells

The invention can be used to efficiently lyse cells contained within a biological matrix. Whole blood or plasma can be drawn into a fluidic passageway by a first microactuator. A solution containing one or more compounds tending to degrade cell walls and membranes, such as guanidine thiocyanate or another protein denaturant, polysorbate 20 or another detergent/emulsifier, and proteinase K or another serine proteinase, may be loaded into a second fluid passageway. The loading of the second fluid passageway with the lysis solution can be preceded by reconstitution of one or more of the lysis solution constituents from a dried-down or lyophilized state. The dried-down or lyophilized material can be in the form of a pellet, can be a plaque-like formation coating a portion of an internal surface of a fluid passageway, or can be distributed in a porous material located within a passageway or chamber.

K. Use with Temperature Controllers

The invention can be used with resistive heaters, with thermoelectric coolers, and with other elements and systems for increasing, decreasing, or regulating temperature of a fluid volume to facilitate reactions.

L. Extraction of DNA and RNA from Complex Starting Samples

The invention can be combined with known methods for reversible binding of DNA, RNA, and other nucleic acids from a starting sample. A solution containing nucleic acids can be caused to flow through a porous structure by the action of a microfluidic actuator. The porous structure can be a packed silica bead bed, such beads being known to reversibly bind nucleic acids. The porous structure can have a pore size distribution and be otherwise configured to capture precipitated material, such as nucleic acids that have precipitated out of solution through binding to glycogen. The flowing of the nucleic acid-containing solution through the porous structure can be preceded by a process in which cells are exposed to compounds which tend to disrupting cell walls and membranes and thereby improve the efficiency of binding to nucleic acids originally contained within cells. The flowing of the nucleic acid-containing solution through the porous structure can be preceded by a process in which some or all of the nucleic acids contained therein bind with a polysaccharide or other substance which causes such sugar-nucleic acid complexes to tend to precipitate. The flowing of the nucleic acid-containing solution through the porous structure can be preceded by a process in which a first microfluidic actuator and a second fluidic actuator, at least one of which is a high performance fluidic actuator, mixes the nucleic acid-containing solution with butanol or another solvent, such that sugar-nucleic acid complexes or other precipitation-prone complexes precipitate out of solution and can be retained near or within the porous structure. The mixing of the solvent and the nucleic acid-containing solution can entail transporting the fluids into a chamber where buoyancy effects associated with the different densities of the solvent and the nucleic acid-containing solution facilitate mixing of the two phases. The mixing of the solvent and the nucleic acid-containing solution can entail transporting the fluids into a chamber where surface tension effects, buoyancy effects, or a combination of these effects causes air bubbles to be retained within such chamber upon withdrawal of the liquid phase or phases from the chamber.

The passing of the nucleic acid-containing solution through the porous structure can be followed by flowing of a solvent such as ethanol through the porous structure to wash away unbound material, such as proteins. There can be more than one such wash step. The passing of a nucleic acid-containing solution through the porous structure can be followed by passing water or another solution tending to reverse binding of nucleic acids, such that nucleic acids will tend to be eluted from the porous structure upon transport of such water or other solution out of said porous structure.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1: Application for HIV Testing

The methods described above can be used to detect or analyze the genetic material or viral proteins of HIV-1 RNA. Because the amount of virus in the bloodstream of even the sickest HIV patient is comparatively small, directly detecting target species requires sophisticated methods.

A starting material including a patient's blood or bodily sample is provided to the microfluidic cartridge. The sample can be processed using a homogenizing solution, beads, or enzymes to lyse the cells in the sample in a fluidic passageway. The homogenizing solution and the sample can be mixed using the microfluidic actuators in the cartridge.

The processed fluid sample can then be mixed with a second fluid by pulsing the fluids together using two or more microfluidic actuators in the microfluidic cartridge. The second fluid can contain reagents such as an antibody, oligonucleotide probe, or labeled molecule that specifically binds to a protein, DNA, RNA or other molecule that is specific to the HIV virus.

Detection of the HIV virus can be performed using any of the detection methods provided above.

Example 2: Detection of Dengue Virus

The methods described above can be used to detect or analyze the genomic material of Dengue virus. Dengue virus (DENV) is a potential biodefense pathogen and is classified as a major international public health concern by the World Health Organization (WHO). Using the microfluidic cartridge and methods described above, the Dengue Virus can be detected in a sample.

A starting material including a patient's blood or bodily sample is provided to the microfluidic cartridge. The sample can be processed using a homogenizing solution, beads, or enzymes to lyse the cells in the sample in a fluidic passageway. The homogenizing solution and the sample are mixed using the Taylor dispersion of plugs of fluid generated by the microfluidic actuators in the cartridge.

Optimized performance of this assay requires operation in the microfluidic cartridge described above. Cartridge-integrated microfluidic actuators drive sample and reagent transport with millisecond temporal resolution, substantially accelerating bead-primer reactions relative to diffusion-limited well-format reactions, while cartridge-integrated heaters control reaction chamber and readout well temperatures with single-degree precision.

Example 3: Detection of *Mycobacterium tuberculosis* (MTB) and Analysis of MTB Genomic Material to Identify Drug Resistant Strains MTB can be identified from a sample or starting material using the above-described methods.

Some strains of MTB are resistant to certain antibiotic drugs widely used to treat MTB. The capacity to identify drug resistance allows the selection of different drugs to treat individuals infected with resistant strains. Examples of MTB resistance of clinical importance include resistance to rifampicin, isoniazid, fluoroquinolones, and pyrazinamide.

A sample, such as a sputum sample, from a patient known to be infected with MTB or suspected to be infected with MTB can be homogenized in a cartridge of this invention and the genomic material, including DNA or ribosomal RNA, released from the bacteria. The sample can then undergo a sequence of steps including the addition of primers to produce a large number of copies of a region of interest, such as the rpoB gene, in a process referred to as isothermal amplification. Action of the microfluidic actuators in the cartridge can rapidly mix probes and primers to cause the isothermal amplification steps to proceed quickly and efficiently. The amplified target can then be labeled, such as with molecular beacons.

Example 4: Quantitation of HIV Virus by Polymerase Chain Reaction (PCR)

The microfluidic cartridge of the invention can be used to precisely determine the quantity of HIV genetic material in a sample of material known or suspected to contain HIV genetic material. Such material can be a whole blood sample, a plasma sample, or other sample. A quantity of sample can be combined with reverse transcription enzymes to facilitate reverse transcription of viral RNA into cDNA. Such combination can be preceded by one or more processes to lyse the viral coating, remove potentially interfering substances, or otherwise prepare the sample for reverse transcription. Such sample preparation can take place within the same cartridge or other microfluidic channel network module as the reverse transcription process, or can take place wholly or in part externally from said cartridge or microfluidic network module. The combination of the material known or suspected to contain HIV genetic material with reverse transcription enzymes can occur at a junction, where the reverse transcription genetic material is in solution form, or can occur through passage of the material into a chamber containing reverse transcription enzymes in lyophilized form, in dried-down form, or in another form. Reconstitution of reverse transcription enzymes in dried-down form, in lyophilized form, or in another form requiring reconstitution can be facilitated by rapid pulsatile flow driven by one or more high performance actuators.

Reverse transcription can occur in a cartridge chamber with associated elements for controlling the temperature of the volume of material in which reverse transcription occurs. Such elements can include resistive heaters, elements for increasing or decreasing the temperature of a mass of material through thermoelectric effects, resistive temperature sensors, circuitry for automatically or manually adjusting the heat production by a heater element as a function of the output of a temperature sensor, and other elements. The solution that has undergone the reverse transcription reaction can be combined with primers, enzymes, and other reagents for polymerase chain reaction. The combination with primers, enzymes, and other reagents can occur through fluid transport, driven by at least one high performance actuator, of the primers, enzymes, and other reagents into the reaction chamber where reverse transcribed DNA was produced, or by fluid transport of the solution containing the reverse transcribed DNA, driven by at least one high performance actuator, into another chamber or more than one other chamber. Amplicon produced by PCR can be detected while the PCR reaction is taking place or by end-point methods. Amplicon produced by PCR can be analyzed by including probes specific for the amplicon with a fluor or other luminescent particle, a quencher particle, and a hairpin structure and which luminesce upon excitation when bound to amplicon. The PCR reaction can be analyzed by changing the temperature of the solution and monitoring binding with labeled probes. The PCR reaction can take place in a plurality of fluid partitions. At least one high performance actuator can facilitate the partitioning of the fluid. The fluid partitions can constitute an emulsion. The volume and number of the partition elements can be chosen to facilitate quantitation through analysis of the fraction of the partition elements found to have contained at least one copy of reverse transcribed DNA prior to the start of the PCR.

Example 5: Detection of Influenza and Other Respiratory Pathogens and Differentiation Among Such Pathogens The invention can be used for melting temperature ($T_m$) analysis of genetic divergence of Influenza A Virus (IAV) RNA from a reference strain. A targeted amplification can be carried out based on possible target identities. The targeted amplification can focus on the HA and NA antigens. The targeted amplification can rapidly classify IAV relative to a reference strain across some or all 8 genome segments. The targeted amplification can incorporate predicted target sequences or can function as an unbiased search for genome-level rearrangement.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A microfluidic cartridge, comprising:
   a plurality of fluid passageways;
   at least one junction connecting said plurality of fluid passageways;

at least two fluidic actuators, including at least one high-performance fluidic actuator being a discrete component within the cartridge and comprising:
- a fluid power generation capacity of at least $10^{-8}$ watts and capable of sustaining said power for at least 30 seconds; and
- a response time for fluid power generation of less than 10 seconds.

2. The cartridge of claim 1, wherein said at least one high-performance fluidic actuator is capable of transducing electrical power into fluidic power.

3. The cartridge of claim 2, wherein said transduction of electrical power into fluid power occurs without an intermediate energy state.

4. The cartridge of claim 1, wherein operation of said at least one high-performance fluidic actuator does not comprise a transfer of mechanical energy from an external device to said at least one high-performance fluidic actuator.

5. The cartridge of claim 1, wherein said response time for power generation is less than 2 seconds, less than 0.2 seconds, or less than 0.04 seconds.

6. The cartridge of claim 1, wherein said actuator is capable of pressurizing at least 10 microliters of liquid, such that said liquid flows through a fluidic resistance associated with a pressure drop of at least 1 kPa at a flow rate of at least 0.1 mL per minute.

7. The cartridge of claim 1, wherein said high-performance actuator is coupled to a controlled time-varying voltage source and at least one electrode.

8. The cartridge of claim 7, wherein said controlled time-varying voltage source is a pulse generator.

9. The cartridge of claim 1, wherein said at least one high-performance fluidic actuator is capable of producing fluidic power through an electrokinetic effect.

10. The cartridge of claim 9, wherein said electrokinetic effect comprises electroosmotic flow.

11. The cartridge of claim 10, wherein said electroosmotic flow is generated within a plurality of slit capillaries within each said at least one fluidic actuator.

12. The cartridge of claim 10, wherein said electroosmotic flow is generated within a bed of packed beads within each said at least one fluidic actuator.

13. The cartridge of claim 10, wherein said electroosmotic flow is generated within a monolithic porous structure within each said at least one fluidic actuator.

14. The cartridge of claim 10, wherein said electroosmotic flow is generated within an array of cylindrical channels within each said at least one fluidic actuator.

15. The cartridge of claim 1, wherein the plurality of passageways comprise a first fluid passageway comprising a first substance and a second fluid passageway comprising a second substance, wherein said first fluid passageway and said second fluid passageway form a junction in said microfluidic cartridge.

16. The cartridge of claim 15, wherein said junction is a T-junction or a Y-junction.

17. The cartridge of claim 16, wherein said one or more droplets each comprise an analyte or a reagent.

18. The cartridge of claim 16, wherein said one or more droplets each comprise at least one primer and an enzyme capable of catalyzing a polymerase chain reaction, a transcription-mediated amplification, a nucleic acid sequence-based amplification, or another chemical reaction for amplifying at least one target nucleic acid sequence.

19. The cartridge of claim 16, wherein said one or more droplets each comprise a label.

20. The cartridge of claim 16, wherein said one or more droplets each comprise a cell.

21. The cartridge of claim 15, wherein said junction allows formation of one or more microfluidic droplets generated from merging of said first and second substances from said first and second fluid passageways.

22. The cartridge of claim 1, wherein said plurality of fluid passageways comprise different temperature zones for performing stages of an amplification reaction.

23. The cartridge of claim 1, wherein a plurality of fluids are combined in said plurality of fluid passageways to trigger a labeling or hybridization reaction.

24. The cartridge of claim 1, wherein said high-performance fluidic actuator comprises:
- a perforated structure with a plurality of slit-like perforations, and
- electrodes on each side of the structure.

25. The cartridge of claim 1, wherein the perforated structure comprises at least one cross-sectional dimension within three orders of magnitude of the characteristic thickness of the electric double layer.

26. The cartridge of claim 1, wherein each of said fluid passageways comprises a piston-like element for contact with a processing fluid, and wherein fluid flow generated by said at least one high-performance fluidic actuator pushes the piston-like element to act on the processing fluid.

27. The cartridge of claim 1, further comprising a network of fluidic passageways in fluid communication with the fluidic actuators.

28. The cartridge of claim 27, further comprising an opening for receiving a processing fluid and coupled to said network of fluid passageways.

29. The cartridge of claim 27, wherein said network of fluid passageways contains a processing fluid.

30. The cartridge of claim 29, wherein said processing fluid comprises a homogenization solution capable of homogenizing a heterogeneous biological material.

31. The cartridge of claim 30, wherein said heterogeneous biological material is a tissue sample.

32. The cartridge of claim 29, wherein said processing fluid comprises a solution capable of diminishing or eliminating biological activity of a living cell, tissue, or organism.

33. The cartridge of claim 29, wherein said processing fluid comprises a glass bead or other solid material capable of causing mechanical disruption of said starting material.

34. The cartridge of claim 27, wherein a portion of said network of fluidic passageways contains a reagent.

35. The cartridge of claim 34, wherein said second reagent comprises a silica bead or a particle, a paramagnetic bead, a fluorescent bead or a fluorescent molecule, or a chemiluminescent molecule.

36. The cartridge of claim 35, wherein said chemiluminescent molecule comprises an alkaline phosphatase substrate.

37. The cartridge of claim 34, wherein said reagent comprises a lanthanide or a lanthanide chelate.

38. The cartridge of claim 34, wherein said reagent comprises a monoclonal or a polyclonal antibody.

39. The cartridge of claim 38, wherein said monoclonal or polyclonal antibody is linked to a signaling molecule.

40. The cartridge of claim 34, wherein said reagent comprises an oligonucleotide probe or primer, a combination of probes, or a combination of primers.

41. The cartridge of claim 40, wherein said oligonucleotide probe specifically binds to a defined region of the genetic material of human immunodeficiency virus.

42. The cartridge of claim 40, wherein said oligonucleotide probe specifically binds to a defined region of the genetic material of hepatitis C virus.

43. The cartridge of claim 40, wherein said oligonucleotide probe specifically binds to a defined region of the genetic material of a hepatitis B virus.

44. The cartridge of claim 40, wherein said oligonucleotide probe specifically binds to a defined region of the genetic material of a *M. tuberculosis* bacterium.

45. The cartridge of claim 40, wherein said oligonucleotide probe specifically binds to a defined region of the genetic material of a *C. trachomatis* bacterium.

46. The cartridge of claim 40, wherein said oligonucleotide probe specifically binds to a defined region of the genetic material of an influenza virus, respiratory syncytial virus, or another virus of the human respiratory tract.

47. The cartridge of claim 40, wherein said oligonucleotide probe specifically binds to a defined region of the DNA or RNA of a cancer gene.

48. The cartridge of claim 40, wherein said oligonucleotide probe is labeled.

49. The cartridge of claim 48, wherein said label comprises a fluorescent or a luminescent signaling molecule or a quencher thereof.

50. The cartridge of claim 40, wherein said oligonucleotide probe comprises an aptamer.

51. The cartridge of claim 34, wherein said reagent comprises a photosensitizer molecule, a photoactive indicator precursor molecule, or both.

52. The cartridge of claim 51, wherein said photosensitizer molecule and said photoactive indicator precursor molecule comprise:

at least one sensitizer label particle comprising one or more sensitizer agents, one or more sensitizer oligonucleotides, and a matrix for co-locating such sensitizer agents and sensitizer oligonucleotide(s); and at least one emitter label particle comprising one or more emitter agents, one or more sensitizer oligonucleotides, and a matrix for co-locating such emitter agent(s) and emitter oligonucleotide(s).

53. The cartridge of claim 52, wherein said photosensitizer molecule is capable in an excited state of generating a singlet oxygen molecule.

54. The cartridge of claim 52, wherein said photoactive indicator precursor molecule is capable of reacting with a singlet oxygen molecule to form a photoactive indicator.

55. The cartridge of claim 34, wherein said reagent comprises a quantum dot or other crystalline semiconductor particle.

56. The cartridge of claim 34, wherein said reagent comprises a nucleic acid-specific fluorescent or luminescent dye for sequence-independent measurement of nucleic acids.

57. The cartridge of claim 34, wherein said reagent comprises a molecule capable of participating in Förster Resonance Energy Transfer (FRET) or other resonance energy transfer process.

58. The cartridge of claim 34, wherein said reagent comprises a labeled protein, a labeled nucleic acid, or a labeled carbohydrate species for measurement of a specific cellular compound.

59. The cartridge of claim 34, wherein said reagent comprises a solution comprises a dye for specific or non-specific labeling of a cell.

* * * * *